US008604222B2

(12) United States Patent
Sheth et al.

(10) Patent No.: US 8,604,222 B2
(45) Date of Patent: Dec. 10, 2013

(54) NEBIVOLOL AND ITS PHARMACEUTICALLY ACCEPTABLE SALTS, PROCESS FOR PREPARATION AND PHARMACEUTICAL COMPOSITIONS OF NEBIVOLOL

(75) Inventors: Rakesh Sheth, Bhat (IN); Srinivasarao Veeravenkata Attanti, Bhat (IN); Hasmukh Mathurbhai Patel, Bhat (IN); Vinodkumar Gupta, Bhat (IN); Sunil Sadanand Nadkarni, Bhat (IN)

(73) Assignee: Forest Laboratories Holdings Limited (BM)

( * ) Notice: Subject to any disclaimer, the term of this patent is extended or adjusted under 35 U.S.C. 154(b) by 1649 days.

(21) Appl. No.: 11/658,979

(22) PCT Filed: Aug. 1, 2005

(86) PCT No.: PCT/IN2005/000252
§ 371 (c)(1),
(2), (4) Date: Mar. 30, 2007

(87) PCT Pub. No.: WO2006/025070
PCT Pub. Date: Mar. 9, 2006

(65) Prior Publication Data
US 2007/0259950 A1 Nov. 8, 2007

(51) Int. Cl.
*C07D 311/00* (2006.01)
*A61K 31/35* (2006.01)

(52) U.S. Cl.
USPC .......................... 549/407; 514/456

(58) Field of Classification Search
USPC .......................... 549/407; 514/456
See application file for complete search history.

(56) References Cited

U.S. PATENT DOCUMENTS

| 4,681,765 | A | 7/1987 | Guley |
| 4,904,477 | A | 2/1990 | Ho et al. |
| 5,948,440 | A | 9/1999 | Arora et al. |
| 6,238,799 | B1 | 5/2001 | Opolski |

FOREIGN PATENT DOCUMENTS

| EP | 0 047 899 | 3/1982 |
| EP | 0145067 | 6/1985 |
| EP | 0 163 984 | 12/1985 |
| EP | 0 334 429 | 9/1989 |
| EP | 0334429 | 9/1989 |
| EP | 0 145 067 | 6/1995 |
| EP | 0744946 | 12/1996 |
| IN | 811/MUM/2004 | 7/2004 |
| WO | 95/22325 | 8/1995 |
| WO | WO 95/22325 | 8/1995 |
| WO | 96/19987 | 7/1996 |
| WO | 01/49268 | 7/2001 |
| WO | 02/087508 | 11/2002 |
| WO | 02/087547 | 11/2002 |
| WO | WO 02/087508 | 11/2002 |
| WO | 2004/039427 | 5/2004 |
| WO | 2005/065639 | 7/2005 |
| WO | 2006/084684 | 8/2006 |

OTHER PUBLICATIONS

FDA-approved BYSTOLIC Prescribing Information, Feb. 2010, pp. 1-5.*
in-PharmaTechnologist.com, New Lutrol Product form BASF, Oct. 16, 2003.pdf.*
BASF—Lutrolmicro brochrure, 2010.*
International Search Report for International Application No. PCT/IN2005/000252 dated Jul. 14, 2006.
Chandrasekhar et al., "Enantioselective Total Synthesis of the Antihypertensive Agent (S, R, R, R)-Nebivolol" Tetrahedron, Elsevier Science Publishers, Amsterdam, NL, vol. 56, No. 34, pp. 6339-6344. Aug. 2000.
Stood, "Kollidon," BASF Erzeugnisse, p. 231, Nov. 1994.
Fiedler, Herben P., Fiedler Lexikon der Hilfsstoffe, Lexicon of the Excipients for pharmacy, cosmetics and adjacent areas, pp. 1393-1394, 2002.
Rompps Chemielexkion, p. 986, 1981.
D.R. Karsa, "Excipients and delivery systems for pharmaceutical formulations", The Royal Society of Chemistry, 1995, pp. 75-82 and 186-188.
Christianah et al., "Povidone", Analytical Profiles of drug substances and excipients, vol. 22, 1993, pp. 555-685.
Amaral, M. Helena et al., "Effect of Hydroxypropyl Methylcellulose and Hydrogenated Caster Oil on Naproxen Release From Sustained-Release Tablets", AAPS PharmSciTech 2001; 2 (2) article 6, (http://www.pharmscitech.org).
"Fiedler Encyclopedia of Excipients for Pharmaceuticals, Cosmetic and Related Areas", edited by Eva-Marie Hoepfner et al., fifth Edition, Editio Cantor Verlag Aulendorf, vol. 9, p. 472, 2002.
Buhler, Vokler, "Kollidon, Polyvinylpyrrolidone for the pharmaceutical industry", Feb. 1999, 4th ed., BASF, Aktiegesellschaft Feinchemie, D-67056, Ludwigshafen.
Tagesson, C., Edling, C., "Influence of Surface-Active Food Additives on the Integrity and Permeability of Rat Intestinal Mucosa", Ed Chem. Toxic, vol. 22, No. 11 pp. 861-864, 1984.

(Continued)

*Primary Examiner* — John Mabry

(57) ABSTRACT

The present invention provides an improved process for the synthesis of nebivolol or its pharmaceutically acceptable salts, more particularly hydrochloride salt of formula (I).

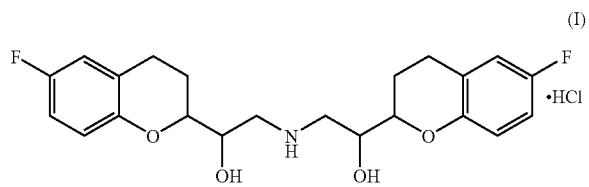

Figure 1:
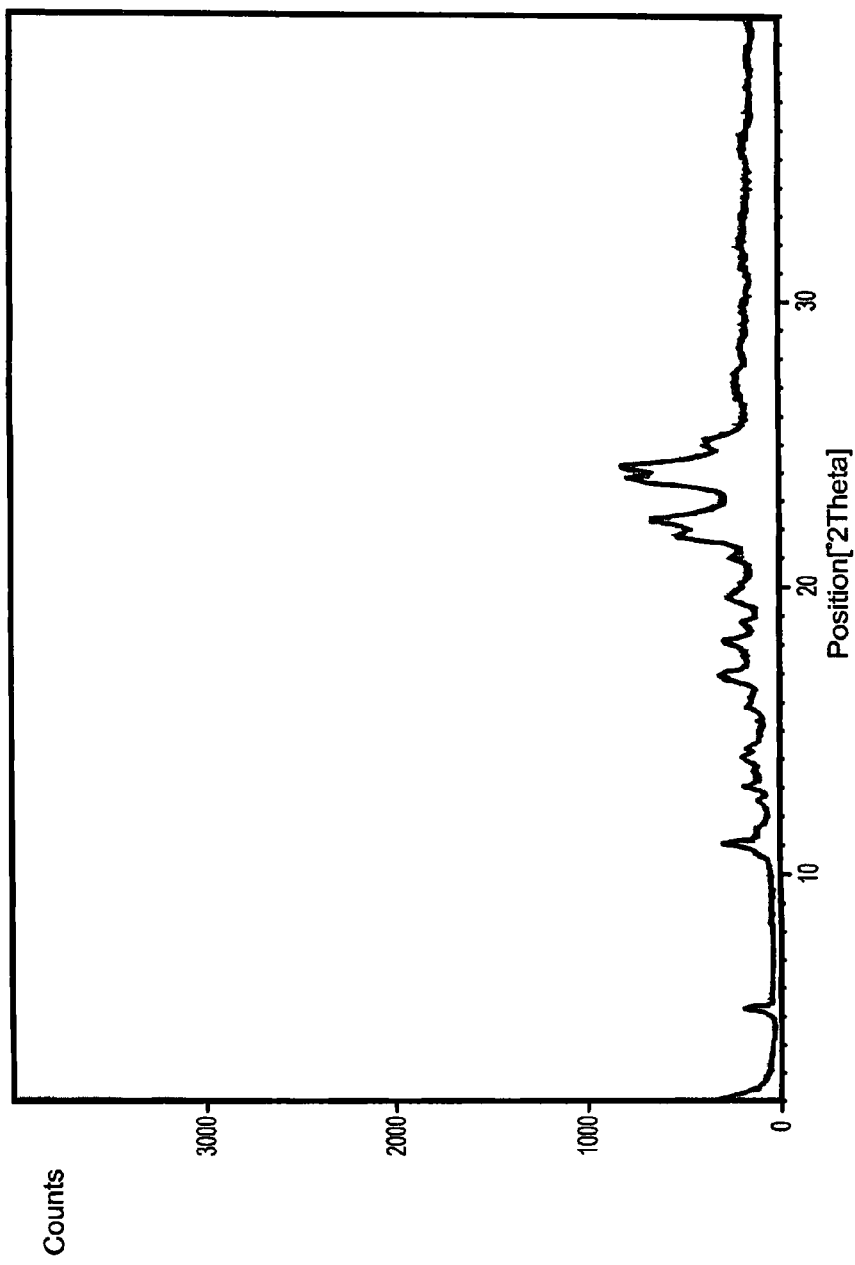

The present invention further provides a new Form T1 of nebivolol and its pharmaceutically acceptable salts.
The present invention also provides pharmaceutical compositions and process for the preparation of a solid oral dosage form of nebivolol hydrochloride of formula (I), without the use of wetting agent, and optionally using binder and/or disintegrant.

6 Claims, 6 Drawing Sheets

(56) References Cited

OTHER PUBLICATIONS

Tiwari, Sandip B., et al. "Controlled Release Formulation of Tramadol Hydrochloride Using Hydrophilic and Hydrophobic Matrix Systems", AAPS PharmSciTech 2003; 4(3) Article 31 (http://www.pharmscitech.org) 6 pages.

Wade et al., "Sodium Lauryl Sulfate" *The Pharmaceutical Press.* Handbook of Pharmaceutical Excipients. Second Edition 1994 pp. 448.

Bermejo et al., "Influence of Synthetic and Natural Surfactants on Drug Passive Permeability in the Gastrointestinal Tract" *Business Briefing* Pharmtech 2003. pp. 1-7.

Swenson et al., Pharm.Res. Aug. 1994; 11(8), pp. 1132-1142 (Abstract only).

Lieberman et al. "Pharmaceutical Dosage Forms: Disperse Systems vol. 1" Second Edition. pp. 261, 1996.

Lieberman et al. "Pharmaceutical Dosage Forms: Disperse Systems vol. 1" Second Edition. pp. 264, 1996.

Food Additives Reference http://www.lactose_co.uk.milkallergy/foodadditives400.html, 2004.

Material Safety Data Sheet Polysorbate 80, 2004.

Reference "Docetaxel" http:www.hci.utah.edu/patientdocs/hci/drugd/docetaxel.htm, 2004.

* cited by examiner

NEBIVOLOL AND ITS PHARMACEUTICALLY ACCEPTABLE SALTS, PROCESS FOR PREPARATION AND PHARMACEUTICAL COMPOSITIONS OF NEBIVOLOL

FIELD OF THE INVENTION

The present invention relates to an improved process for the synthesis of pharmaceutically active 2,2'-iminobisethanol derivative i.e., 2H-1-benzopyran-2-methanol,α,α'-iminobis (methylene)]bis[6-fluoro-3,4-dihydro-,[2R*[R*[R*(S*)]]]] i.e., nebivolol or its pharmaceutically acceptable salts, more particularly hydrochloride salt (I).

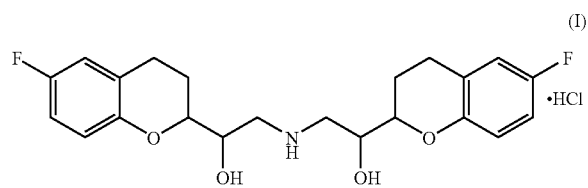 [SMILES: OC(CNCC(O)C1CCc2cc(F)ccc2O1)C1CCc2cc(F)ccc2O1 ; "·HCl"]

(I)

Nebivolol is useful in the treatment and prevention of coronary vascular disorders.

The present invention also relates to pharmaceutical compositions and process for the preparation of a solid oral dosage form of nebivolol hydrochloride of formula (I), without the use of wetting agent, and optionally using binder and/or disintegrant.

The present invention further provides a new polymorphic form of nebivolol hydrochloride.

BACKGROUND OF THE INVENTION

Beta-blockers are used for the treatment of high blood pressure, control of angina, arrhythmia, post myocardial infection, heart failure, migraine or essential tremor.

Nebivolol is a highly selective beta-1 blocker and has been found to be useful for the management of hypertension. Hypertension (high blood pressure) is a significant health risk affecting more than 500 million people across the world and needs long-term therapy for its management.

Chemically nebivolol is 2,2'-iminobisethanol derivative i.e., 2H-1-benzopyran-2-methanol,α,α'-[iminobis(methylene)]bis[6-fluoro-3,4-dihydro-,[2R*[R*[R*(S*)]]]]. EP 744 946 B1 discloses nebivolol to be a mixture of equal amounts of 2 enantiomers having respectively the SRRR- and the RSSS-configuration.

Methods for preparation of nebivolol are disclosed in EP-0145067 and EP-0334429. EP 0145067 B1 describes a process for the conversion of 6-fluoro-3,4-dihydro-2H-1-benzopyran-2-carboxaldehyde (VI) into isomeric mixtures of 6-fluoro-3,4-dihydro-2-oxiranyl-2H-1-benzopyran (VII). This reaction entails the use of sodium hydride as the base, which is extremely hazardous. Further, purity of the product, i.e., 6-fluoro-3,4-dihydro-2-oxiranyl-2H-1-benzopyran (VII) obtained by using sodium hydride is low and is found to be around 62-65%, which is unacceptable. The mixture of oxiranes represented by the formula (VII) are separated by column chromatography as shown in Scheme (I) to obtain A-isomer of (VII) (i.e., VII-A) from the first fraction and B-isomer of (VII) (i.e., VII-B) from the second fraction.

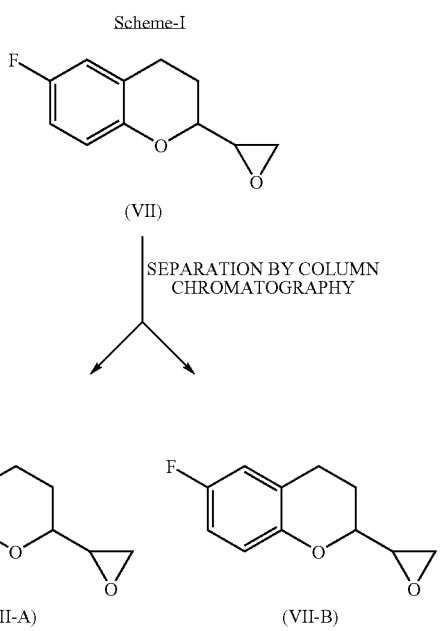

The A-isomer of (VII) is then treated with benzylamine to obtain the benzylated A-isomer of (VII) (i.e., Intermediate I), which is reacted with the B-isomer in presence of oxalic acid to obtain the oxalate salt of benzylated nebivolol (VIII-a), as shown in Scheme-II.

Furthermore, the oxalate salt (VIII-a) as obtained has to be treated with an alkali to obtain the free benzylated nebivolol base (VIII).

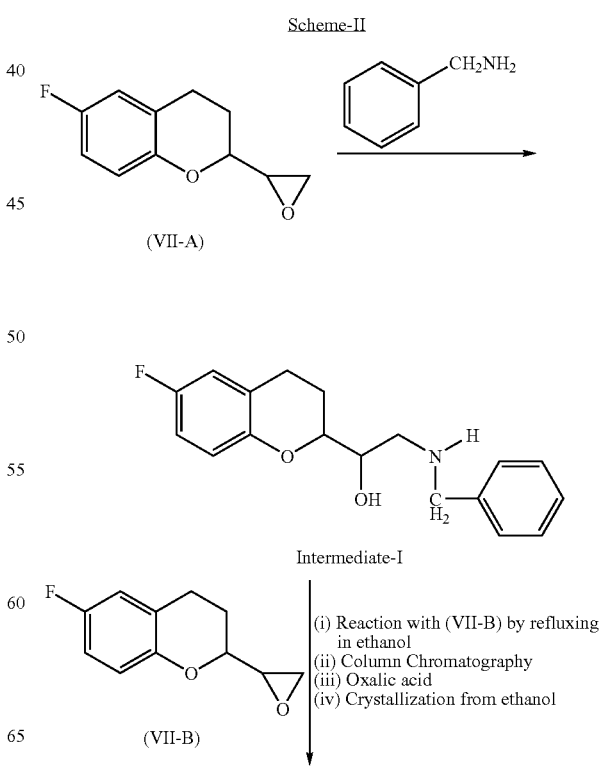

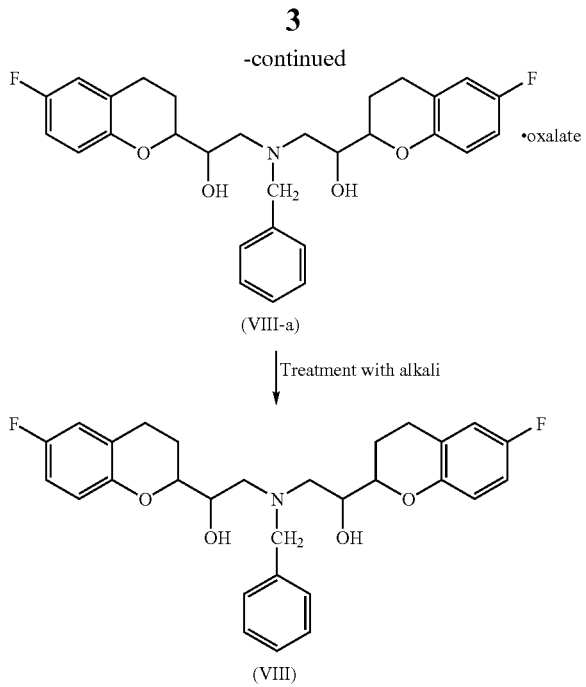

Thus, as can be seen from Scheme II, the reaction between Intermediate-I and (VII-B) involves purification by column chromatography, and subsequent treatment with oxalic acid to form the oxalate salt. Treatment with oxalic acid results in the separation of the undesired (RSRR+SRSS) diastereomers from the desired (RSSS+SRRR) isomers, due to a difference in solubilities between the desired and the undesired isomers. Further, the oxalic acid salt has to be converted to the free benzylated nebivolol base by treatment with an alkali. The multiple steps in the process make it cumbersome and lead to increase in utilities and in the manufacturing time cycle of the active pharmaceutical ingredient. Moreover the purity of the free benzylated nebivolol base is also found to be relatively low.

EP 334429 B1 discloses a process for the preparation of specifically the RSSS isomer of nebivolol independently. The said process for the independent preparation of RSSS nebivolol involves the use of hazardous reagents like thionyl chloride, sodium hydride and di-isobutyl aluminium hydride (DIBAL), expensive optically active reagents like (+)-1,2,3,4,4a,9,10,10a-octahydro-1,4a-dimethyl-7-(1-methylethyl-1-phenathrenemethanamine[(+)-dehydroabiethylamine] and utilities like column chromatography and low temperatures. The processes also involve a large number of steps thereby increasing in utilities, manpower and time required to complete the production cycle, rendering the process commercially expensive.

Furthermore, EP 744946B1 describes a process for obtaining nebivolol hydrochloride from a mixture containing the desired (RSSS+SRRR) nebivolol base contaminated by the undesired (RSRR+SRSS) diastereomers, using ethanol as both the reaction as well as the recrystallization solvent. The major disadvantage of the said process is that it uses impure nebivolol base as the starting material containing different isomeric impurities, and thereby results in a very low yield (6.6%) of the desired isomers (having the SRRR- and the RSSS-configuration) of nebivolol hydrochloride. Moreover, ethanol is a solvent that can be used only in controlled quantities due to stringent regulatory requirements, and therefore its use on an industrial scale is limited.

Thus, there exists a need for developing a method for the synthesis of the desired diastereomeric mixture of higher purity with the reduction of undesirable isomeric impurities and eliminating the use of hazardous sodium hydride, while at the same time reducing the process steps in the synthesis of nebivolol.

It has been surprisingly found that the process of synthesizing nebivolol in accordance with the process of the present invention not only increases the purity of the desired diastereomeric mixture in a minimum number of process steps but also eliminates the use of hazardous chemicals in the process.

Nebivolol is mainly used for the treatment and prevention of coronary vascular disorders. It is taken once or twice a day as per the requirement of the patient.

EP 0744946 discloses pharmaceutical compositions of nebivolol where the drug is in micronized form and with the addition of one or more wetting agents specifically polysorbates as an adjuvant. This patent emphasizes the need of micronization and further wetting as the oral administration of nebivolol hydrochloride is impeded by the poor dissolution when in a normal crystalline form. In order to achieve a good dissolution the active ingredient has to be sufficiently wetted.

The micronization of nebivolol hydrochloride as required in EP 0744946 B1 for preparing pharmaceutical compositions unjustifiably increases the time cycle for the manufacturing process. It also requires undue utilities like milling and sifting, which increases the cost of preparing the final product. It is further demonstrated that on comparison of dissolution of tablets comprising crystalline versus micronized nebivolol, the dissolution rate of the tablet comprising crystalline nebivolol (Example 6 of EP 744946) is less than 50% after 45 minutes.

EP 0145067 B1 provides pharmaceutical composition of derivatives of 2,2'-iminobisethanol for various dosage forms i.e. oral drops, injectable solution, oral solution, film coated tablets and the like. The use of sodium dodecyl sulfate is disclosed in EP 0145067 B1 in the preparation of film-coated tablet. Sodium dodecyl sulfate, i.e., sodium lauryl sulfate, (Wade, A. and Weller P. J., *Handbook of Pharmaceutical Excipients*, $2^{nd}$ ed., 1994, page 448) is a wetting agent in the core of the composition (film coated tablet).

WO 2002/087508 discloses nitrosated and nitrosylated nebivolol and its metabolites and pharmaceutical composition using the same. It is disclosed that the bio-availability of the composition can be enhanced by micronization of the formulation using conventional techniques such as grinding, milling, spray drying and the like in the presence of suitable excipients or agents such as phospholipids or surfactants.

Thus, the existing literature reveals that attempts to use the natural crystalline form of nebivolol have resulted in poor dissolution rate and poor bioavailability. Attempts for combining the crystalline form with a wetting agent are also largely unsuccessful. For achieving appropriate dissolution rate or bioavailability of nebivolol hydrochloride, micronized nebivolol is needed. The micronization process is both cost extensive and time consuming, and requires the use of wetting agent.

Wetting agent is a surfactant, a substance capable of reducing the surface tension of a liquid in which it is dissolved. The effect of surfactant over the intestinal membrane is more complex. It has been shown that most surfactants interact with the absorbing membranes (Bermejo, D. M. and Ruiz-Garcia, A., Business Briefing: Pharmatech 2003; pages 1-7). Permeability enhancement and local damage are closely related sequelae of the interaction of surfactants with the intestinal wall (Swenson, E. S., Milisen, W. B., Curatolo, W., *Pharm. Res.* 1994 August; 11(8), pages 1132-42). Ingested surfactants may facilitate penetration or absorption of potentially toxic or pathogenic compounds, which in turn may result in adverse effects on the other organs (Lieberman, H. A., Rieger, M. M. and Banker, G. S., Eds., *Pharmaceutical Dosage Forms: Disperse Systems,* $2^{nd}$ ed, Vol. 1, page 261). The surfactant can facilitate their own entry and that of other material into the body, which thus enters in to the systemic circulation (Lieberman, H. A., Rieger, M. M. and Banker, G. S., Eds., *Pharmaceutical Dosage Forms: Disperse Systems,* $2^{nd}$ ed., Vol. 1, page 264).

Polysorbate 60 or 80 affects the integrity of intestinal mucosa (Lieberman, H. A., Rieger, M. M. and Banker, G. S., Eds., *Pharmaceutical Dosage Forms: Disperse Systems,* $2^{nd}$ ed., Vol. 1, page 261). Polysorbate 80 may increase the absorption of fat-soluble substances.

Management of hypertension being a long term therapy, use of wetting agents in the formulation of nebivolol need to be judiciously avoided. Large doses of polysorbate 80 as a wetting agent in pharmaceutical formulations produces abdominal spasms, diarrhea. Further, polysorbate 80 containing pharmaceutical compositions have found to cause allergy in various patients. Polysorbate 20 and polysorbate 40 should also be avoided in formulations as they are banned in certain countries.

Thus there is a long felt need to have compositions of nebivolol that are safe and efficacious at the same time being cost and time effective for manufacturing.

The present inventors have surprisingly found that pharmaceutical compositions of the present invention prepared using nebivolol as the active ingredient and without using wetting agent, exhibited excellent dissolution characteristics that were also found to be comparable with respect to the marketed formulation.

It was further surprisingly found that nebivolol hydrochloride could be formulated not only without the use of wetting agent but optionally without using binder or disintegrant without retarding the dissolution characteristics of the drug.

OBJECTS OF THE INVENTION

It is thus an object of the present invention to provide for an improved process for the synthesis of pharmaceutically active 2,2'iminobisethanol derivative i.e. 2H-1-benzopy ran-2-methanol,α,α'-iminobis(methylene)]bis[6-fluoro-3,4-dihydro-,[2R*[R*[R*(S*)]]]] i.e. nebivolol base or its hydrochloride salt of formula (I) above.

Another object of the present invention is to provide a simple and economical process for synthesis of nebivolol base or its hydrochloride salt that involves minimum number of process steps and does not utilize hazardous chemicals in the synthesis.

Yet another object of the present invention is to provide pharmaceutical compositions comprising nebivolol hydrochloride active ingredient and one or more adjuvants, without incorporating wetting agent, to achieve desired dissolution profile.

A further object of the present invention is to provide process to manufacture solid dosage form as tablets or capsules in a simple and cost effective manner.

Yet another object of the present invention is the preparation of a solid dosage form of nebivolol hydrochloride, and one or more adjuvants, without the use of wetting agent optionally without using binder and optionally without using disintegrant.

Another object of the present invention is to provide a novel polymorphic form of nebivolol and its pharmaceutically acceptable salts in particular hydrochloride salt and its process of preparation.

Another object of the present invention is to provide use of the pharmaceutical composition of nebivolol hydrochloride of the instant invention prepared without using wetting agent for the treatment of hypertension.

SUMMARY OF THE INVENTION

Thus according to a first aspect of the present invention there is provided an improved process for the synthesis of pharmaceutically active 2,2'iminobisethanol derivative i.e. 2H-1-benzopyran-2-methanol,α,α'-iminobis(methylene)]bis[6-fluoro-3,4-dihydro-,[2R*[R*[R*(S*)]]]] i.e. nebivolol or its hydro halide more particularly nebivolol hydrochloride salt, as shown in Figure (I),

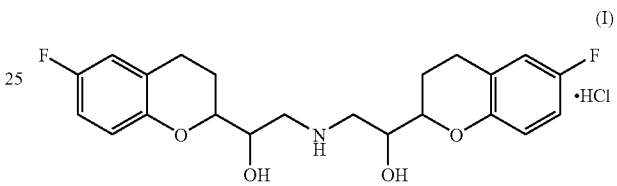

(I)

wherein

6-Fluoro-3,4-dihydro-2H-1-benzopyran-2-carboxaldehyde (VI) is converted to isomeric mixture of oxiranes represented by formula (VII), in presence of potassium tertiary butoxide as a base, and the reaction between the benzylated A-isomer of (VII) (i.e., Intermediate I) and the B-isomer (VII-B) and isolation of the reaction product is carried out in presence of an organic solvent in controlled time and temperature conditions, leading to the formation of the free benzylated nebivolol base (IX).

According to second aspect of the present invention, there is provided nebivolol synthesized by the process of the present invention.

According to another aspect of the present invention, there are provided pharmaceutical compositions of nebivolol comprising nebivolol or its pharmaceutically acceptable salts formulated without using wetting agents.

Further, the present invention also provides a solid dosage form of nebivolol hydrochloride, and one or more adjuvants, without the use of wetting agent, optionally without using binder and/or disintegrant and a process for preparation of the same.

According to yet another aspect of the present invention, there are provided a process for manufacturing the pharmaceutical composition of the present invention In yet another aspect of the present invention, there is provided a novel polymorphic form of nebivolol and its pharmaceutically acceptable salts.

In another embodiment of the invention, the preferred specific surface area of the nebivolol hydrochloride is $0.2 \times 10^3$ $m^2/kg$ to $1.95 \times 10^3$ $m^2/kg$.

DETAILED DESCRIPTION

The present invention accordingly provides for an improved process for the preparation of 2H-1-benzopyran-2-methanol,α,α'[iminobis(methylene)]bis[6-fluoro-3,4-dihydro-,[2R*[R*[R*(S*)]]]] i.e. nebivolol of formula (IX) or its pharmaceutically acceptable salts like the hydrochloride salt as shown in formula (I).

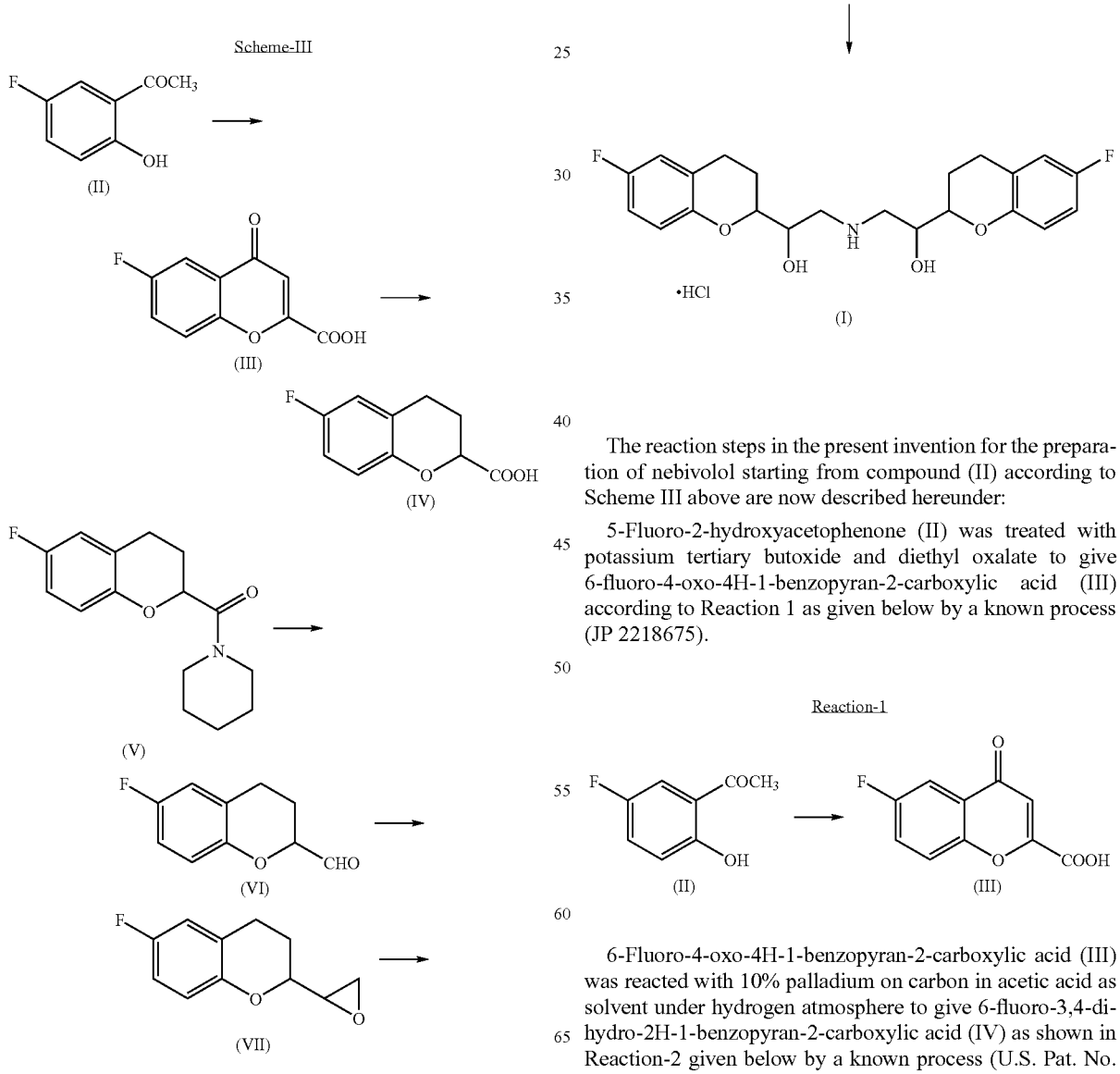

Nebivolol is prepared according to the present invention by the synthetic route shown in Scheme III given below:

The reaction steps in the present invention for the preparation of nebivolol starting from compound (II) according to Scheme III above are now described hereunder:

5-Fluoro-2-hydroxyacetophenone (II) was treated with potassium tertiary butoxide and diethyl oxalate to give 6-fluoro-4-oxo-4H-1-benzopyran-2-carboxylic acid (III) according to Reaction 1 as given below by a known process (JP 2218675).

Reaction-1

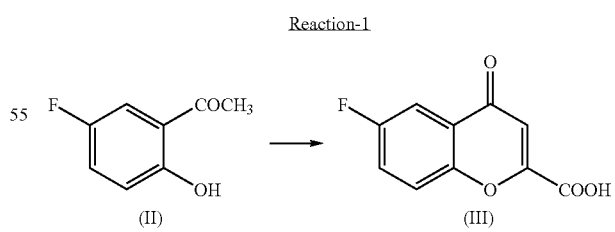

6-Fluoro-4-oxo-4H-1-benzopyran-2-carboxylic acid (III) was reacted with 10% palladium on carbon in acetic acid as solvent under hydrogen atmosphere to give 6-fluoro-3,4-dihydro-2H-1-benzopyran-2-carboxylic acid (IV) as shown in Reaction-2 given below by a known process (U.S. Pat. No. 4,654,362).

Reaction-2

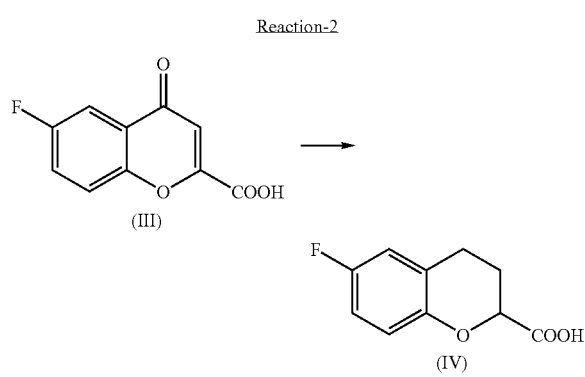

6-Fluoro-3,4-dihydro-2H-1-benzopyran-2-carboxylic acid (IV) is converted into the amide (V-A) using amine RR'NH and acid activating agent as indicated in Reaction 3(a), Reaction 3(a)

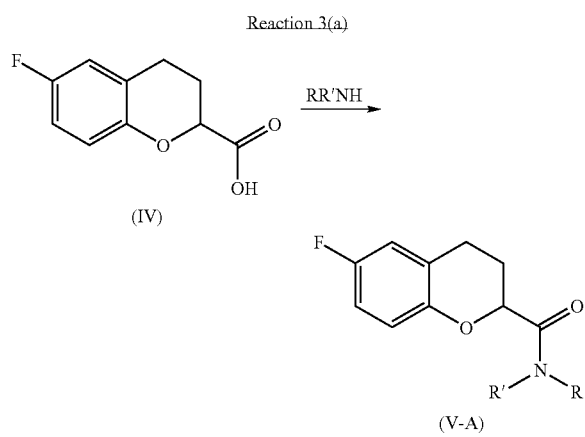

wherein, R and R' are independently H, alkyl or phenyl, optionally joined together with or without a heteroatom such as O, N or S. Alkyl is straight chain or branched $C_1$ to $C_6$ alkyl.

In the Reaction 3 (a) of formation of amide (V-A) from acid (IV), the amine RR'NH can be selected from the group of primary or secondary amines. The primary amine is selected from aliphatic or aromatic primary amine, whereas the secondary amine is selected from cyclic secondary amines or non-cyclic secondary amines, wherein substitution on nitrogen is independently aliphatic or aromatic or combination thereof.

Preferably, secondary amines can be used. More preferably, secondary amines, which are cyclic amines are used.

The amines can be selected from the group comprising of dimethylamine, diethylamine, N-methylphenylamine, pyrrolidine, piperidine, N,O-dimethylhydroxylamine and morpholine. The preferred amine is piperidine.

The activating agent according to Reaction-3 (a) is selected from the group comprising of thionyl chloride, ethylchloroformate, acetic anhydride, phosphorus trichloride, phosphorus oxychloride, phosphorus pentachloride, dicyclohexylcarbodiimide, N,N'-carbonyldiimidazole and chlorosaccharin. The preferred activating agents are thionyl chloride and ethylchloroformate.

In a preferred embodiment, 6-Fluoro-3,4-dihydro-2H-1-benzopyran-2-carboxylic acid (IV) was converted into 6-fluoro-3,4-dihydro-2H-1-benzopyran-2-carboxylic acid piperidine amide (V) using thionyl chloride and piperidine in toluene as solvent, as indicated in Reaction-3 below.

Reaction-3

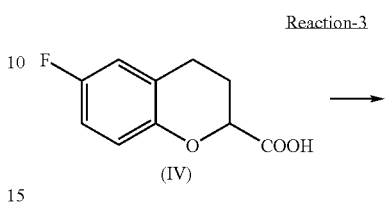

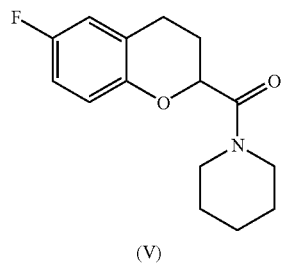

The reduction of amide (V-A) to give 6-fluoro-3,4-dihydro-2H-1-benzopyran-2-carboxaldehyde of Formula (VI) is carried out by using an alkoxy metallic hydride wherein, alkoxy group is substituted or unsubstituted —O($C_1$-$C_4$) alkyl, and substitution if any, by —O($C_1$-$C_4$)alkyl and, metallic part contains metal selected from the group comprising of Li or Na.

Reaction 4(a)

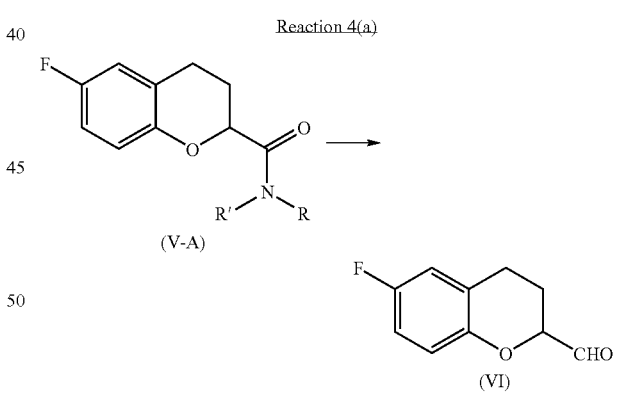

The alkoxy metallic hydride reducing agent is selected from the group comprising of sodium bis(2-methoxyethoxy) aluminium hydride, lithium diethoxyaluminum dihydride and lithium tri-tert-butoxy aluminium hydride.

The preferred reducing agent is sodium bis(2-methoxyethoxy) aluminium hydride.

6-Fluoro-3,4-dihydro-2H-1-benzopyran-2-carboxylic acid piperidine amide (V) was reduced by using vitride i.e. Sodium bis(2-methoxyethoxy)aluminium hydride in toluene to give 6-fluoro-3,4-dihydro-2H-1-benzopyran-2-carboxaldehyde (VI) as given below in Reaction-4.

Reaction-4

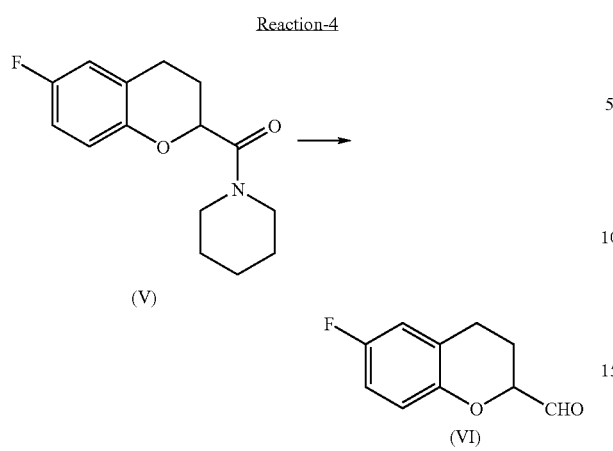

6-Fluoro-3,4-dihydro-2H-1-benzopyran-2-carboxaldehyde (VI) was reacted with trimethyl sulfoxonium iodide in presence of base, potassium tertiary butoxide and solvent dimethyl sulfoxide to give isomeric mixture of oxiranes represented by formula (VII), which may be optionally distilled, as indicated in Reaction-5.

Reaction-5

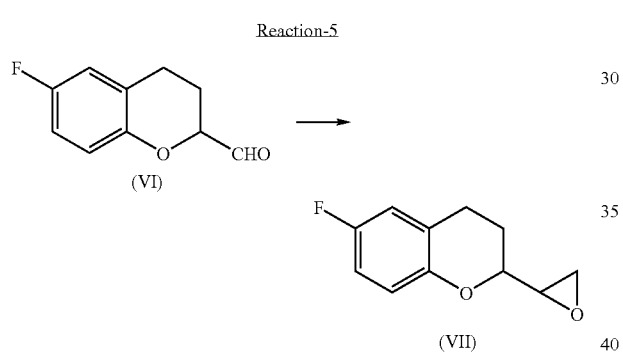

Thus, the present invention avoids the use of sodium hydride as base in the above reaction. Due to the said change of the above base, the purity of the reaction product, i.e., oxirane (VII) is substantially higher. The purity of the oxirane obtained by using potassium tertiary butoxide as base is above 75% before product distillation, compared to a purity of 60-65% of the product before product distillation obtained in our hand by using sodium hydride base, as per the procedure described in EP 0145067 B1. The process of the present invention affords the advantage of both avoiding the use of hazardous sodium hydride as well as improving the purity of the oxirane.

The mixture of oxiranes was separated by column chromatography to elute firstly pure fraction (A-isomer i.e. VII-A), i.e. (A)-6-fluoro-3,4-dihydro-2-oxiranyl-2H-1-benzopyran of EP 0 145 067. Further, upon elution the second fraction (B-isomer i.e. VII-B), i.e. (B)-6-fluoro-3,4-dihydro-2-oxiranyl-2H-1-benzopyran of EP 0 145 067 was obtained.

The chromatographic separation of two isomers A and B was carried out (EP 0 145 067) (Scheme-I) using silica gel as the stationary phase whereas the eluant is the mixture of hexanes and ethyl acetate. If the loading material is in higher quantity, the purification by column chromatography can be done simultaneously on multiple columns (more than one column). The column chromatography yielded Isomer-A in the beginning, followed by Isomer-B. Based on the purity of the fractions from the column, they can be mixed together and used for further reaction.

Scheme-I

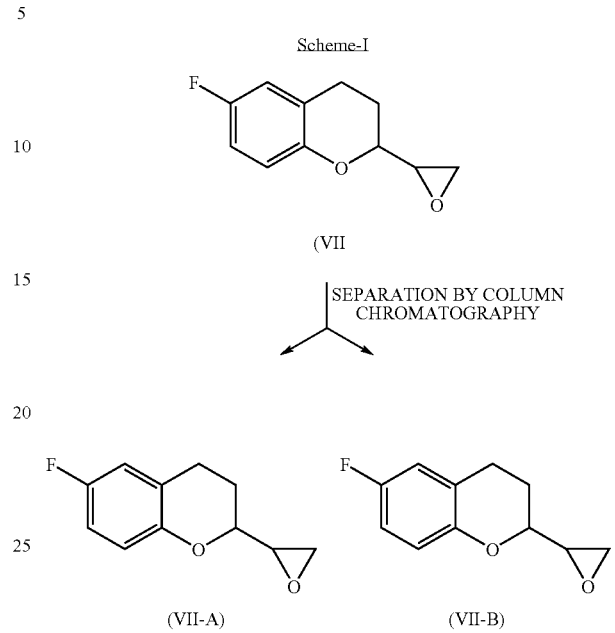

(A)-6-fluoro-3,4-dihydro-2-oxiranyl-2H-1-benzopyran (VII-A) was reacted with benzylamine in isopropyl alcohol to give (A)-6-fluoro-3,4-dihydro-alpha-[[(phenylmethyl)amino]-methyl]-2H-1-benzopyran-2-methanol (Intermediate I), by a known process (U.S. Pat. No. 4,654,362), as indicated in Reaction-6.

Reaction-6

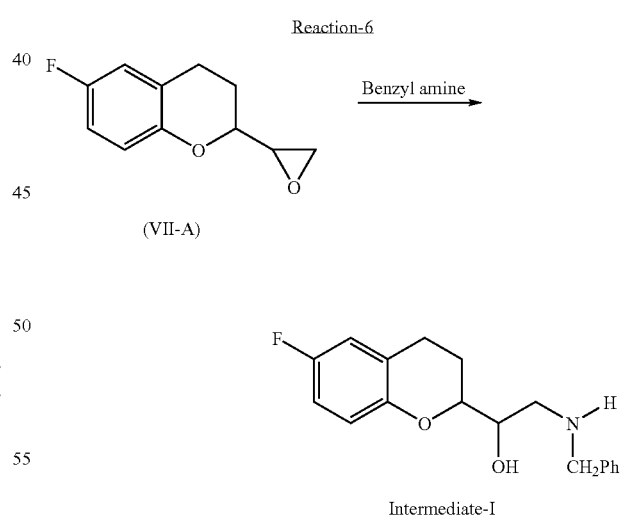

(A)-6-Fluorodihydro-α-[[(phenylmethyl)amino]-methyl]-2H-1-benzopyran-2-methanol (Intermediate-1) was reacted with (B)-6-fluoro-3,4-dihydro-2-oxiranyl-2H-1-benzopyran (VII-B) in presence of an organic solvent and isolated at a temperature of −5 to −25° C., and maintaining the reaction mass at the temperature of isolation for more than 2 hours to give benzylated nebivolol as shown in the following Reaction-7.

Reaction-7

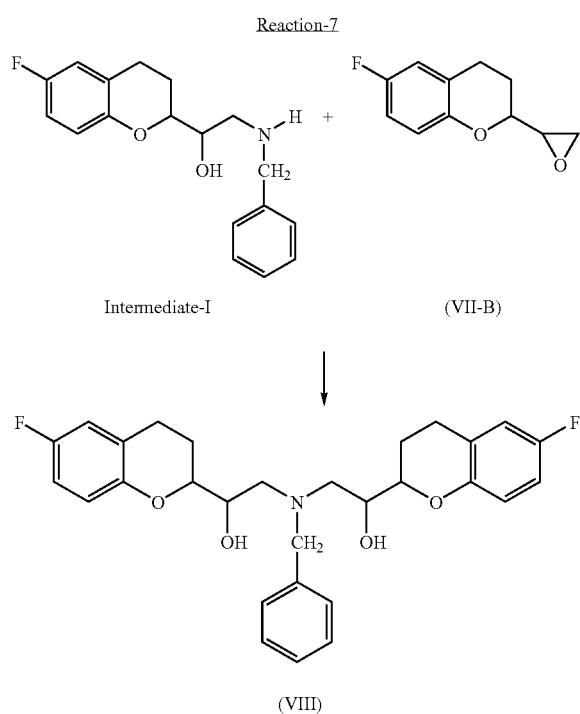

In the present invention, the reaction between the benzylated A-isomer of (VII) (i.e., Intermediate I) and the B-isomer (VII-B) was carried out in an organic solvent and isolated at a temperature of −5 to −25° C. leading directly to the formation of the free benzylated nebivolol base (IX) containing only the desired isomers (having SRRR- and RSSS-configuration). It has been observed surprisingly in the present invention, that the isolation when carried out a low temperature, particularly at a temperature of −5 to −25° C. yields substantially pure desired stereoisomers, (HPLC purity >90.0%) which can be further optionally purified in alcoholic solvent such as methanol, ethanol to get desired stereoisomer in highly pure form (HPLC purity >98.5%), as compared to the process described in the prior art, wherein the desired isomers are obtained with considerably less purity (HPLC purity <60.0%) even after repetitive purification of oxalate salt of benzylated nebivolol.

The organic solvent as used in Reaction-7 is selected from the group comprising of alcohols, esters, ketones and acetonitrile.

In one embodiment of the invention, the alcohol is selected from the group comprising of methanol, ethanol, isopropyl alcohol, n-propyl alcohol, n-butanol, isobutanol. In a preferred embodiment, the alcohol used is methanol. In another embodiment, the esters are selected from the group comprising of ethyl acetate, n-butyl acetate. In a further embodiment, the ketones are selected from the group comprising of acetone, methyl ethyl ketone, methyl isobutyl ketone (MIBK).

The isolation is carried out a temperature range of −5 to −25° C., preferably at a range of −10 to −20° C., and more preferably at a range of −10 to −15° C.

The reaction mass is maintained at the temperature of isolation for a period of 2-40 hours, preferably for a period of 4-30 hours, more preferably for a period of 8-20 hours, and most preferably for a period of 10-15 hours.

Thus, the process of the present invention has the following advantages:
(i) Avoids the use of column chromatography,
(ii) Avoids preparation of oxalate salt and recrystallization steps thereof, and,
(iii) Avoids subsequent conversion of the oxalate salt to free benzylated nebivolol base by treatment with an alkali.

Therefore, compared to prior art processes, the process of the present invention leads to a decrease in the number of process steps, thereby making it more economical and time effective.

Further, the hydrogenation reaction was carried out using 10% palladium on carbon for debenzylation reaction of the benzylated nebivolol base (VIII) to give nebivolol base (IX), by a known process (U.S. Pat. No. 4,654,362) as given in the following Reaction 8.

Reaction-8

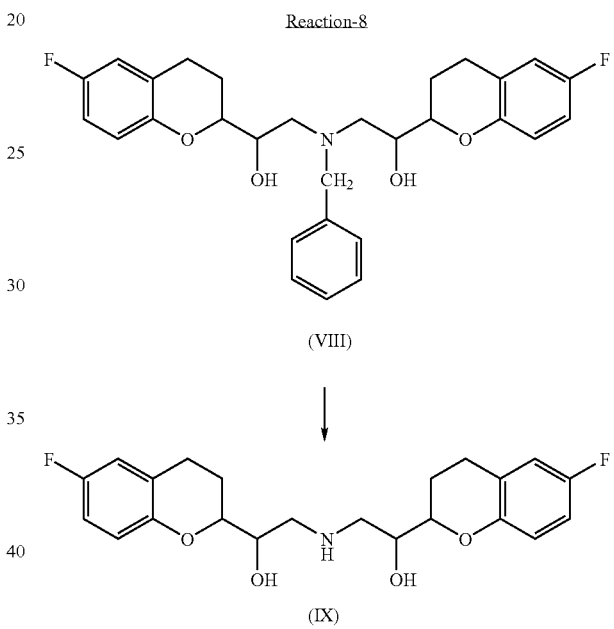

Nebivolol may be converted into its pharmaceutically acceptable acid addition salt forms by treatment with appropriate acids. Appropriate acids are, for example, inorganic acids, such as hydrohalic acid, e.g., hydrochloric, hydrobromic, sulfuric acid, nitric acid, phosphoric acid; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methybenzenesulfonic, cyclohexanesulfamic, 2-hydroxybenzoic, 4-amino-2-hydroxybenzoic acids. In a preferred embodiment, the acid addition salt is hydrochloride.

Nebivolol base (IX) was converted into nebivolol hydrochloride (I) using an organic solvent and hydrochloric acid (Reaction 9). It was observed in the present invention that the preparation of nebivolol hydrochloride in alcohols/esters/ketones gives near quantitative yield of the product compared to other organic solvents. The present process for the conversion of nebivolol base to nebivolol hydrochloride salt in the presence of alcohol as solvent leads to product with near quantitative yields. Thus, by the process of the present invention, nebivolol hydrochloride containing only the desired isomeric mixture can be prepared in high yield.

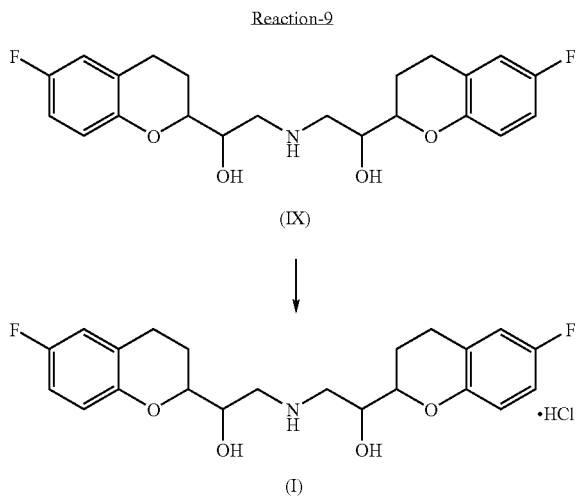

The solvents for conversion into nebivolol hydrochloride or even further purification can be selected from the group consisting of alcohols, esters, ketones, halogenated solvents, acetonitrile and water or mixtures thereof. In one embodiment of the invention, the alcohol used for the conversion can be selected from the group comprising of methanol, ethanol, n-propanol, isopropanol, n-butanol, isobutanol and the like. In another embodiment, the ester can be selected from the group comprising of ethyl acetate, n-butyl acetate and the like. In yet another embodiment, the ketone can be selected from acetone or methyl isobutyl ketone (MIBK). In another embodiment, halogenated solvents such as methylene dichloride, can be used for conversion of nebivolol base into nebivolol hydrochloride.

Also, nebivolol hydrochloride can be prepared by reacting nebivolol base and alcoholic hydrogen chloride such as methanolic HCl, ethanolic HCl, n-propanolic HCl, isopropanolic HCl, n-butanolic HCl.

Also, the same can be achieved by passing HCl gas through the solution of nebivolol base, wherein the solvent used can be as mentioned above.

Nebivolol Hydrochloride Form T1

The present invention also provides a novel amorphous form of nebivolol and its pharmaceutically acceptable salts designated as Form T1.

Polymorphism is the occurrence of distinct crystalline forms of a single compound, and have the same molecular formula, but each polymorph may have distinct physical properties. A single compound may give rise to a variety of polymorphic forms, whose physical properties may be distinct and different, such as different solubility profiles, different melting point temperatures and different x-ray diffraction peaks. Due to differing solubility profiles of polymorphs, the identification of pharmaceutical polymorphs is essential for preparing pharmaceutical dosage forms with predictable solubility profiles.

The term "amorphous" as used herein denotes a physical state, which is not crystalline and may be verified by X-ray diffraction, infrared spectroscopy and other means including but not limited to observation with a polarized light microscope and differential scanning calorimetry.

The term "pharmaceutically acceptable salt" as used herein refers to salts which are known to be non-toxic and are commonly used in the pharmaceutical literature. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenylsubstituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, beta-hydroxybutyrate, chloride, cinnamate, citrate, formate, fumarate, glycolate, heptanoate, lactate, maleate, hydroxymaleate, malonate, mesylate, nitrate, oxalate, phthalate, phosphate, monohydro genphosphate, dihydrogenphosphate, metaphosphate, pyrophosphate, propionate, phenylpropionate, salicylate, succinate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

In one particularly preferred embodiment, the invention provides the hydrochloride salt of nebivolol, in an amorphous form.

The said amorphous form can be obtained by techniques such as spray drying. Freeze drying and the like.

In a preferred embodiment the said form is obtained by conventional spray drying technique using a LabPlant SPD-005® spray drier. Nebivolol hydrochloride is dissolved in alcohol such as methanol under heating to obtain a clear solution or adjust pH below 2.0 of nebivolol base solution/suspension in alcohol using aqueous HCl/Alcoholic HCl/HCl gas, which is then spray dried for a period of 2 to 5 hours, and further isolating nebivolol hydrochloride Form T1.

The term "isolating" comprises filtration, drying, or any other techniques known to the person skilled in art. The alcohol used for the preparation of Nebivolol hydrochloride Form T1 is selected from the group comprises of methanol, ethanol, propanol, isopropanol, n-butanol, and the like and its mixtures thereof.

BRIEF DESCRIPTION OF THE ACCOMPANYING DRAWINGS

FIG. 1: This figure indicates X-ray diffraction pattern of partially amorphous Form T1 of nebivolol hydrochloride obtained according to the present invention.

Figure 2:
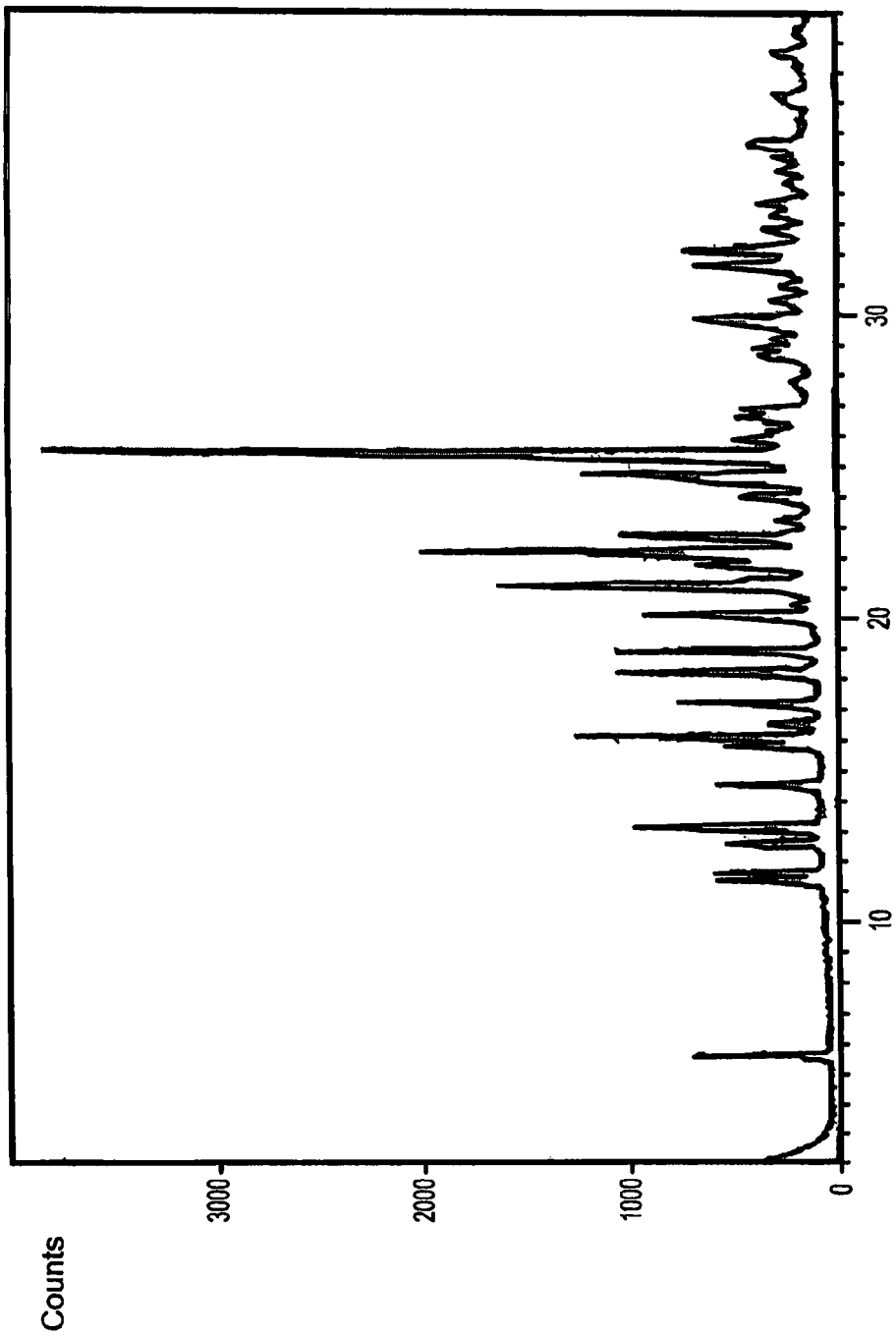

FIG. 2: This figure indicates X-ray diffraction pattern of the crystalline form of nebivolol hydrochloride obtained by reported process (EP0145067).

Figure 3:
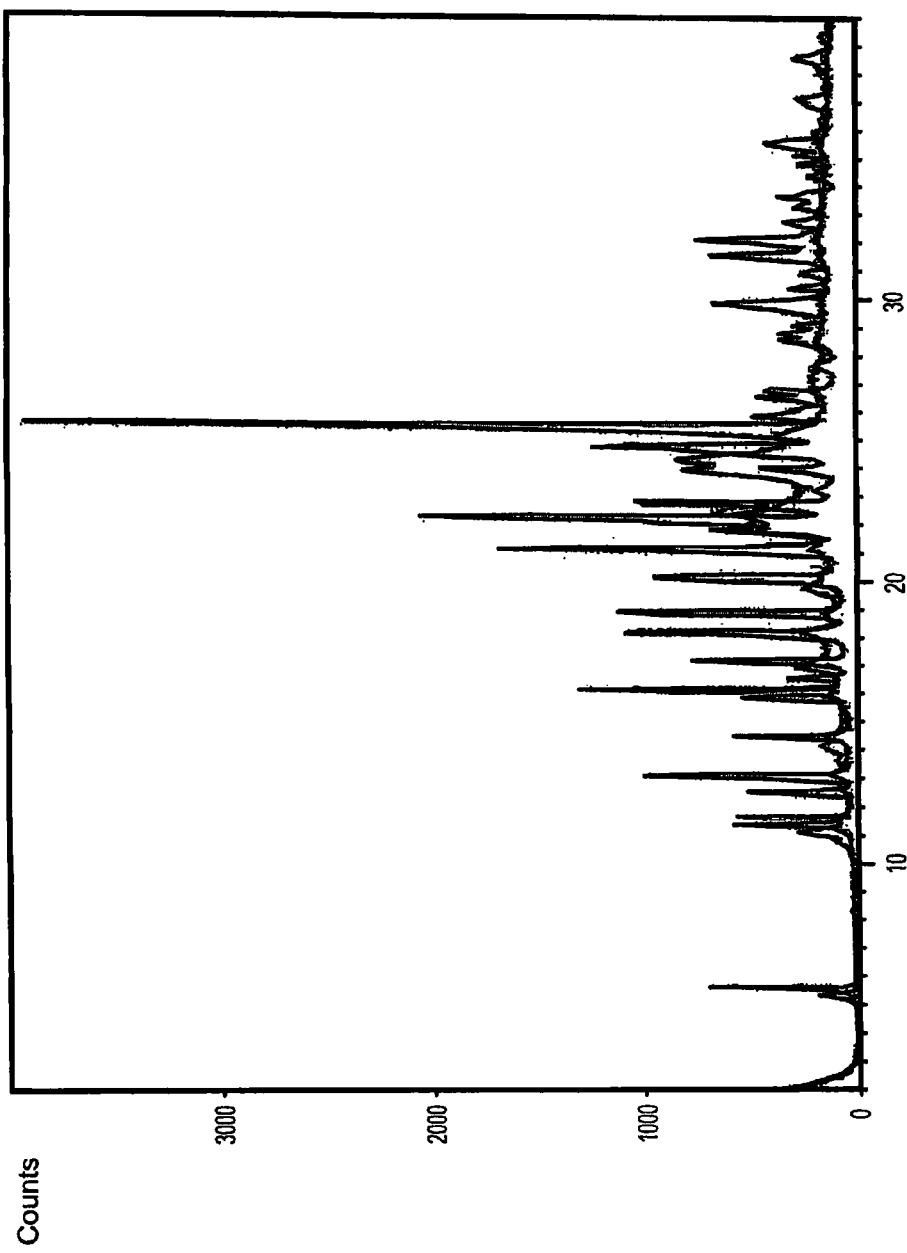

FIG. 3: This figure indicates comparative and superimposed X-ray diffraction pattern of form T1 and crystalline form of nebivolol hydrochloride obtained according to present invention.

Figure 4:
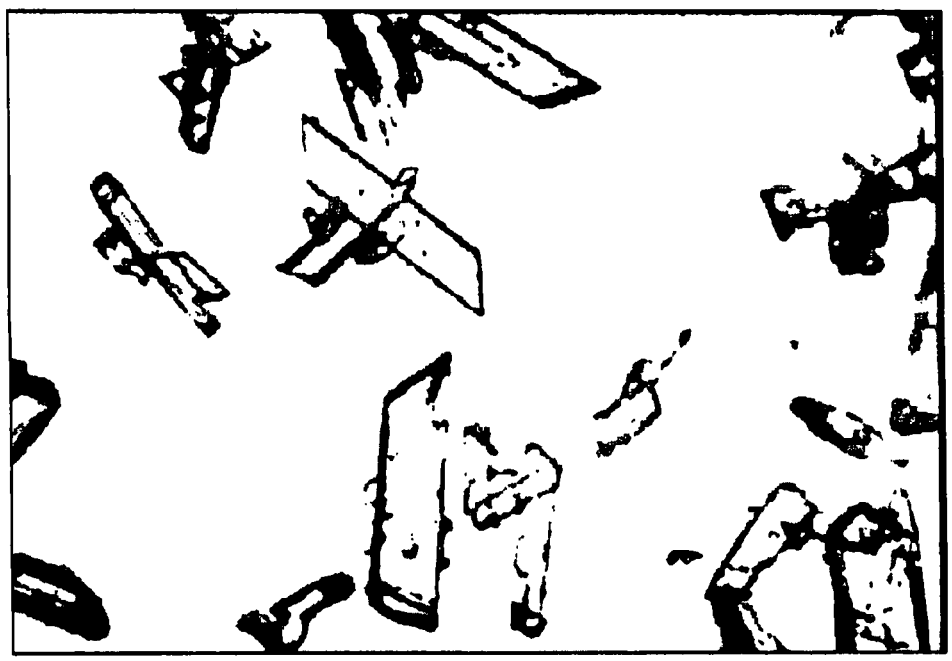

FIG. 4: This photograph is a microscopic image of crystalline nebivolol hydrochloride taken using AXIOLAB microscope.

Figure 5:
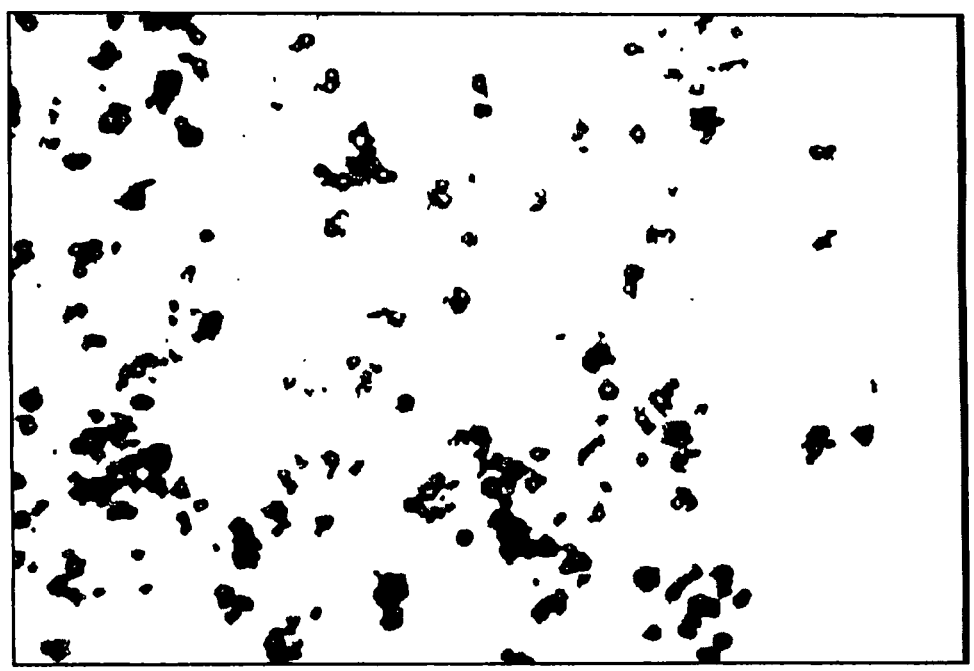

FIG. 5: This photograph is a microscopic image of spray dried nebivolol hydrochloride taken using AXIOLAB microscope.

Figure 6:
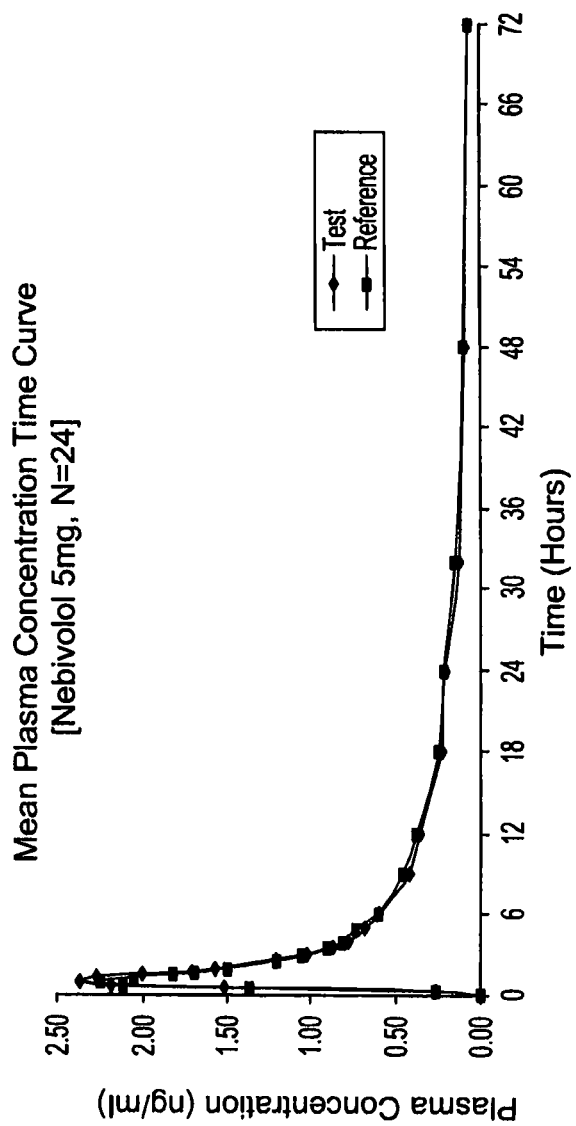

FIG. 6: Mean plasma concentration time curve of nebivolol test v/s reference formulation.

CHARACTERIZATION OF NEBIVOLOL HYDROCHLORIDE FORM T1

The Form T1 of nebivolol hydrochloride of formula (I) is characterized by the following data:

Nebivolol hydrochloride Form T1 is characterized by powder X-ray diffraction (XRPD) pattern as depicted in FIG. 1, and can be differentiated from the crystalline form by X-ray powder diffraction angles (2θ, degrees), d-values, and relative intensities, as set out in Table 1 given below:

TABLE 1

| Form T1 | | | Crystalline Form | | |
|---|---|---|---|---|---|
| Diffraction Angle ± 0.2° (degree two theta) | Lattice Spacing (D) (Angstroms) | Relative Intensity (%) | Diffraction Angle ± 0.2° (degree two theta) | Lattice Spacing (D) (Angstroms) | Relative Intensity (%) |
| 5.43 | 16.26 | 27.42 | 5.70 | 15.50 | 16.73 |
| 11.15 | 7.93 | 38.76 | 11.43 | 7.73 | 13.77 |
| 12.68 | 6.97 | 6.58 | 11.67 | 7.57 | 13.25 |
| 13.20 | 6.70 | 18.15 | 12.62 | 7.01 | 11.39 |
| 14.24 | 6.21 | 16.27 | 13.15 | 6.73 | 24.02 |
| 14.57 | 6.07 | 12.98 | 14.56 | 6.08 | 13.16 |
| 15.91 | 5.56 | 10.79 | 15.87 | 5.58 | 11.95 |
| 16.91 | 5.24 | 22.17 | 16.15 | 5.48 | 30.72 |
| 17.11 | 5.18 | 28.88 | 16.54 | 5.35 | 6.65 |
| 18.24 | 4.86 | 24.50 | 17.20 | 5.15 | 15.41 |
| 18.90 | 4.69 | 7.86 | 18.19 | 4.87 | 26.89 |
| 19.77 | 4.49 | 22.49 | 18.93 | 4.68 | 26.43 |
| 21.18 | 4.19 | 8.59 | 20.19 | 4.39 | 21.31 |
| 21.82 | 4.07 | 50.82 | 20.58 | 4.31 | 1.92 |
| 22.51 | 3.94 | 73.21 | 21.14 | 4.20 | 39.13 |
| 23.85 | 3.73 | 82.08 | 21.84 | 4.06 | 14.09 |
| 24.39 | 3.64 | 100.00 | 22.25 | 3.99 | 49.17 |
| 25.17 | 3.53 | 28.34 | 22.75 | 3.90 | 23.75 |
| 27.29 | 3.26 | 6.40 | 23.32 | 3.81 | 3.45 |
| 28.69 | 3.11 | 4.94 | 24.05 | 3.70 | 8.56 |
| 35.59 | 2.52 | 6.40 | 24.54 | 3.62 | 15.30 |
| | | | 24.77 | 3.59 | 27.45 |
| | | | 25.41 | 3.50 | 100.00 |
| | | | 25.90 | 3.43 | 8.83 |
| | | | 26.23 | 3.39 | 4.18 |
| | | | 26.60 | 3.34 | 8.15 |
| | | | 26.88 | 3.31 | 7.69 |
| | | | 27.71 | 3.21 | 1.79 |
| | | | 28.62 | 3.11 | 5.30 |
| | | | 28.86 | 3.09 | 5.71 |
| | | | 29.15 | 3.06 | 3.85 |
| | | | 29.81 | 2.99 | 13.19 |
| | | | 30.46 | 2.93 | 3.67 |
| | | | 30.89 | 2.89 | 2.16 |
| | | | 31.56 | 2.83 | 13.74 |
| | | | 32.09 | 2.78 | 15.18 |
| | | | 32.81 | 2.72 | 4.31 |
| | | | 33.32 | 2.68 | 3.50 |
| | | | 33.63 | 2.66 | 5.25 |
| | | | 34.28 | 2.61 | 1.74 |
| | | | 34.71 | 2.58 | 2.87 |
| | | | 35.04 | 2.56 | 2.97 |
| | | | 35.45 | 2.53 | 6.77 |
| | | | 35.63 | 2.51 | 5.89 |
| | | | 36.89 | 2.43 | 2.95 |
| | | | 37.17 | 2.41 | 4.25 |
| | | | 38.54 | 2.33 | 3.82 |
| | | | 39.34 | 2.28 | 0.94 |

The Form T1 of nebivolol hydrochloride is differentiated from the crystalline form with the following differentiation:

Absence of the peaks at about 11.67±0.2, 16.54±0.2, 22.75±0.2, 25.41±0.2, 29.81±0.2, 31.56±0.2, 32.09±0.2 degrees two-theta.

Conspicuous presence of the peaks at 5.4330±0.2, 11.1544±0.2 & 19.7730±0.2 degrees two-theta.

Pharmaceutical Composition

The present invention also provides a process for preparation of solid dosage form preferably tablet or capsule of nebivolol hydrochloride (I) and one or more adjuvants, without the use of wetting agent. Further the present invention also provides the solid dosage form of nebivolol hydrochloride, and one or more adjuvants, without the use of wetting agent, optionally without using binder and optionally without using disintegrant and process for preparation of the same.

Pharmaceutical composition according to the present invention is preferably in the form of a tablet or capsule. The active ingredient used in the present pharmaceutical composition is nebivolol hydrochloride, which may be optionally sieved through mesh #100.

The solid dosage form tablet or capsule of the present invention is prepared using active ingredient i.e., nebivolol hydrochloride and pharmaceutically acceptable excipients selected from the group comprising of diluents, disintegrants, binders, lubricants, glidants and other pharmaceutically acceptable excipients or adjuvants but not wetting agent.

Diluents can be selected from the group comprising of lactose, starch, dibasic calcium phosphate anhydrous, tribasic calcium phosphate, kaolin, sucrose, mannitol, precipitated calcium carbonate, sorbitol, maltodextrin, cellulose derivatives including powdered cellulose, micro crystalline cellulose and other materials known to one of ordinary skill in the art.

Binders can be selected from the group comprising of polyvinylpyrrolidone or hydroxypropylmethylcellulose, acacia, alginic acid, hydroxy propyl cellulose, carboxymethylcellulose sodium, compressible sugar, ethylcellulose, gelatin, liquid glucose, methylcellulose, pregelatinized starch and other materials known to one of ordinary skill in the art.

Disintegrants can be selected from the group comprising of starch, sodium starch glycolate or croscarmellose sodium, crospovidone, alginic acid, carboxymethyl cellulose sodium, Guar gum and other materials known to one of ordinary skill in the art.

Lubricants can be selected from the group comprising of stearic acid, polyethylene glycol, magnesium stearate, calcium stearate, talc, zinc stearate, hydrogenated castor oil, silica, colloidal silica, cornstarch, calcium silicate, magnesium silicate, silicon hydrogel and other materials known to one of ordinary skill in the art.

Glidants can be selected from the group comprising of colloidal silicon dioxide, colloidal silica, cornstarch, talc, calcium silicate, magnesium silicate, colloidal silicon, silicon hydrogel and other materials known to one of ordinary skill in the art.

Other pharmaceutical solvents are selected from the group comprising of methanol, acetone and purified water.

The preferred specific surface area of the nebivolol hydrochloride according to the present invention is between $0.2 \times 10^3$ m$^2$/kg and $1.95 \times 10^3$ m$^2$/kg.

The composition of the present invention comprises the ingredients in the following proportion. Quantity of nebivolol or its pharmaceutically acceptable salt can be based upon the requirement of human dosage.

TABLE 2

| Sr. No. | Ingredient in the present invention | Minimum (%) | Maximum (%) |
|---|---|---|---|
| 1. | Nebivolol or its pharmaceutically acceptable salt | 0.5 | 10.00 |
| 2. | Diluent | 78.00 | 93.05 |
| 3. | Binder (optional) | 0.5 | 5.00 |
| 4. | Disintegrant(optional) | 0.5 | 10.00 |
| 5. | Lubricant | 0.25 | 3.00 |
| 6. | Glidant | 0.25 | 3.00 |

The solid dosage form of the present invention containing nebivolol or its pharmaceutically acceptable salt is prepared according to the following steps:

(I) a. Prepare powder blend by passing lactose, starch and croscarmellose sodium through mesh #60 and further mixing it.
    b. Prepare the solution of nebivolol or its pharmaceutically acceptable salt and hydroxypropyl methylcellulose or povidone in methanol or a suitable solvent and water.
    c. Adsorb the solution from above step (b) onto the dry mix diluents of step 1 (a).
    d. Dry the resultant of step (c) above and granulate with water.
    e. Dry the wet granules at 60° C. and sieve the dried granules though #30 mesh
    f. Lubricate the granules of step (e) with croscarmellose sodium, colloidal silicon dioxide, microcrystalline cellulose and magnesium stearate and mix in a blender.
    g. Compress the granules obtained in step (IV) into tablets or fill the granules into capsules.

OR (I) Nebivolol or its pharmaceutically acceptable salt, lactose, starch and croscarmellose sodium are passed through mesh #60 and mix it properly.
(II) Prepare binder solution using hydroxy propyl methylcellulose or povidone in aqueous or non-aqueous granulating solvents.
(III) Granulate the powder mixture of step (I)-c OR (I') with a binder solution prepared in step II in a high speed mixer and dry the granules in a fluid bed dryer.
(IV) Lubricate the granules of step (III) with croscarmellose sodium, colloidal silicon dioxide, microcrystalline cellulose and magnesium stearate and mix in a cage blender.
(V) Compress the granules obtained in step (IV) into tablets or fill the granules into capsules.

Thus, by using the above simple and less expensive method, dissolution achieved is at least 75% in 45 minutes without the use of wetting agent as shown in the relevant examples.

Throughout this specification and the appended claims it is to be understood that the words "comprise" and "include" and variations such as "comprises", "comprising", "includes", "including" are to be interpreted inclusively, unless the context requires otherwise. That is, the use of these words may imply the inclusion of an element or elements not specifically recited.

The details of the invention, its objects and advantages are explained hereunder in greater detail in relation to non-limiting exemplary illustrations. The examples are merely illustrative and do not limit the teaching of this invention and it would be obvious that various modifications or changes in the procedural steps as well as compositions by those skilled in the art without departing from the scope of the invention and shall be consequently encompassed within the ambit and spirit of this approach and scope thereof.

EXAMPLES

Example 1

Preparation of 6-fluoro-3,4-dihydro-2H-1-benzopyran-2-carboxylic acid piperidine amide (V)

120 ml of toluene and 0.8 ml of dimethyl formamide were added to 40 g of 6-fluoro-3,4-dihydro-2H-1-benzopyran-2-carboxylic acid (IV) under stirring at room temperature. Thionyl chloride (32 g) was added and the reaction mixture heated to 60-70° C. and maintained for 30 min. Thionyl chloride and toluene were distilled out under reduced pressure. To the reaction mixture, 160 ml of toluene was further added and cooled. To this, 88 ml of piperidine was slowly added at room temperature and stirred for 30 min. The reaction mixture was acidified using dilute HCl. The aqueous layer was extracted with toluene and the combined organic layers washed with dilute HCl followed by water. The organic solvent was removed under reduced pressure to obtain 40 g of the title compound as a solid.

Alternatively, the following procedure can as well be used. To 100 g of 6-fluoro-3,4-dihydro-2H-1-benzopyran-2-carboxylic acid (IV), 1500 ml of methylene chloride and 70 g of triethylamine were added at 20° to 40° C. The reaction mixture was cooled to 0° to −5° C. and 57 g of ethylchloroformate was slowly added over a period of 30 to 45 minutes. The reaction mixture was maintained at 0° to −5° C. for 1 h. Subsequently, 55 g of piperidine was added over a period of 30 to 45 minutes, while maintaining the temperature at 0° to −5° C. The reaction mixture was maintained at 0° to 5° C. for 1.5 h. till completion of the reaction. 1 lit of water was added at 0° to 5° C. and the pH adjusted to 2.0 with concentrated hydrochloric acid at 15° to 20° C. Stirred for 0.5 hr and the layers were separated. The methylene chloride layer washed with 2 lit of water, and then distilled out the methylene chloride completely under vacuum at the temperature up to 45° C. 200 ml of hexane was added and distilled out completely. Again 200 ml of hexane was added and stirred at 20° to 40° C. for 0.5 h and cooled to 0°-5° C. Maintained at 0°-5° C. for 1 h, filtered and washed with 100 ml of chilled hexane at 0°-5° C. to give 110 g dry weight (dried at 55° to 60° C. in hot air oven for 6 hours) of the title compound as a solid.

Example 2

Preparation of 6-fluoro-3,4-dihydro-2H-1-benzopyran-2-carboxaldehyde (VI)

To 40 g of amide (V) was added 400 ml of toluene. To it, vitride solution (mixture of 44 g vitride in toluene) was slowly added at 10 to 15° C. Methanol was added to the reaction mixture which was then acidified using dilute HCl. The reaction mixture was extracted with toluene and concentrated under reduced pressure to provide 26 g of the title compound.

Example 3

Preparation of 6-fluoro-3,4-dihydro-2-oxiranyl-2H-1-benzopyran (VII)

To 234 ml of dimethyl sulfoxide was added 32 g of trimethyl sulfoxonium iodide. To it, potassium tertiary butoxide (16 g) was added and stirred for 1 h at 20-40° C. The reaction mixture was cooled and to it was added a solution of the compound obtained in Example 2 in dimethyl sulfoxide (26 ml.) while maintaining the temperature between 20°-40° C. for 1.5 hr. The reaction mixture was quenched in cold water. The aqueous layer was extracted with ethyl acetate, washed with water, concentrated under reduced pressure followed by product distillation to give 19.6 g of 6-fluoro-3,4-dihydro-2-oxiranyl-2H-1-benzopyran (VII) in the form of a mixture of A and B as an oil.

The mixture of isomer A (VII-A) and isomer B (VII-B) were separated by column chromatography using silica gel as the stationary phase and a mixture of hexane and ethyl acetate as eluant. 6.75 g of the mixture of isomers A and B was eluted with a mixture of hexane:ethyl acetate (in the ratio 97:3), till Isomer A separates out completely. The column is further eluted with a mixture of hexane:ethyl acetate (in the ratio 90:10), to get Isomer B. The eluates of Isomer A and Isomer B were evaporated to get respectively 2.6 g of isomer A (VII-A) as an oil and 1.4 g of isomer B (VII-B).

% Purity obtained: 78-82%

Example 4

Preparation of (A)-6-fluorodihydro-α-[[(phenylmethyl)amino]-methyl]-2H-1-benzopyran-2-methanol (Intermediate-I)

10.65 g of isomer A (VII-A) was added to 31.9575 ml of isopropyl alcohol followed by addition of 7.13 g. of benzylamine. The reaction mixture was heated to reflux for 2 hr and chilled to 0-5° C. The solid was filtered and purified with isopropyl alcohol (27 ml) to give 8.52 g of the title compound.

Example 5

Preparation of Benzylated Nebivolol Base (VIII)

10 g of Isomer B (VII-B) and 14.70 g of A amine (Intermediate-I) were added to 50 ml of methanol and heated to 65-70° C. The reaction mass was maintained at the same temperature for 15 h. The mass was then cooled to 50-55° C., to which 30 ml of methanol was added. It was further cooled to −10 to −15° C. and stirred at the same temperature for 12 h. The material was filtered, washed with 5 ml of methanol at −10 to −15° C., filtered and dried at 40-45° C. for 8 h to obtain 11.5 g of the title compound.

Example 6

Preparation of Nebivolol Base (IX)

Benzylated nebivolol base (VIII) (5.85 g) along with 2-methoxy ethanol (117 ml) and 0.351 g palladium on carbon (10%) was added to the hydrogenator. 160-170 psi pressure applied with hydrogen gas and heated it to 70-75° C. The temperature and pressure conditions were maintained for 3 hrs till the completion of reaction. The reaction mass cooled to room temperature and filtered through (18 g) hyflow bed to separate the catalyst.

The filtrate was evaporated to get solids, isolated the solids in methanol (38 ml) at 0-5° C. The solid was dried to get 4.0 g of nebivolol base.

Example-7

Preparation of Nebivolol HCl (I) Using Methanol as Reaction Solvent and Purification of Nebivolol HCl (I)

70 ml of methanol and 3.5 g of hydrochloric acid were added to 10 g of nebivolol base (IX) and the reaction mixture was stirred for 4 h at 28-32° C. The material was filtered & washed with chilled methanol. It was subsequently filtered to dryness. The wet material was refluxed in 300 ml of methanol for 30 min and then filtered through a hyflow bed. The methanol was distilled out completely and to the residue, 100 ml of isopropyl alcohol was added and further stirred for 30 min at 60-65° C. Cooled to 25-30° C. The material was again stirred at 28-32° C. for 3 hrs. The material was filtered, washed with 20.0 ml of isopropyl alcohol and dried at 60-65° C. for 8 hrs to obtain 10.5 g of nebivolol hydrochloride (I).

m.p. range: 223-227° C.

Yield (%): 96.33%

HPLC Purity: 99.89%

Example-8

Preparation of Nebivolol HCl (I) Using Isopropyl Alcohol as Reaction Solvent and Purification of Nebivolol HCl (I)

70 ml of isopropyl alcohol and 3.5 g of hydrochloric acid were added to 10 g of nebivolol base (IX) and the reaction mixture was stirred for 4 h at 28-32° C. The material was filtered, washed with 10.0 ml of isopropyl alcohol and filtered to dryness. The wet material was refluxed in 300 ml of methanol for 30 min and then filtered through a hyflow bed. The methanol was distilled out completely and to the residue, 100 ml of isopropyl alcohol was added and stirred for further 30 min at 60-65° C. Cooled to 28-32° C. Stirred the material at 28-32° C. for 3 hrs, filtered & washed with 20.0 ml of isopropyl alcohol and dried at 60-65° C. for 8 hrs to obtain 10.6 g of nebivolol hydrochloride (I).

m.p. range: 223-227° C.
Yield (%): 97.24%
HPLC Purity: 99.16%

Example-9

Preparation of Nebivolol HCl (I) from Nebivolol Base (IX) Using Ethanol as Reaction Solvent and Purification of Nebivolol HCl (I)

70 ml of ethanol and 3.5 g of hydrochloric acid were added to 10 g of nebivolol base (IX) and the reaction mixture was stirred for 4 h at 28-32° C. The material was filtered, washed with 10.0 ml of ethanol and filtered to dryness. The wet material was refluxed in 300 ml of methanol for 30 min and then filtered through a hyflow bed. The methanol was distilled out completely and to the residue, 100 ml of isopropyl alcohol was added and stirred for further 30 min at 60-65° C. Cooled to 28-32° C., stirred the material at 28-32° C. for 3 hrs, filtered & washed with 20.0 ml of isopropyl alcohol and finally dried at 60-65° C. to obtain 10.5 g of nebivolol hydrochloride (I). Further, the material is sieved through mesh #100.

m.p. range: 223-227° C.
Yield (%): 96.33%
HPLC Purity: 99.45%

Example-10

Preparation of Nebivolol Hydrochloride (I) from Benzylated Nebivolol Base (VIII)

Benzylated nebivolol base (40.0 g) along with 2-methoxy ethanol (300 ml) and 10% Palladium on Carbon (6.0 g) were added to the hydrogenator. 160-170 psi pressure was applied with hydrogen gas and heated to 70-75° C. The temperature & pressure conditions were maintained for 3.0 h and the completion of the reaction checked by TLC/HPLC. The reaction mixture was cooled to room temperature and filtered through hyflow bed to separate the catalyst. The filtrate was heated to 65-70° C. with subsequent addition of 14.0 ml of hydrochloric Acid (35%). The reaction mass was stirred for 2.0 h. The material was filtered followed by addition of methanol (800.0 ml) and heated to 60-65° C. to get a clear solution. Filtered over a hyflow bed. The filtrate was distilled under vacuum till the volume remains 20%. The reaction mass was then cooled to 0-5° C. and stirred at the same temperature for 2.0 h. The material was filtered and dried at 55-60° C. to obtain 28.0 g of the title compound.

HPLC Purity: 99.99%

Example-11

Preparation of Form T1

To 2100 ml of methanol was added 60.0 g of nebivolol hydrochloride at room temperature. The reaction mass was heated to 50-60° C. to obtain a clear solution. The clear solution was spray-dried for a period of 3.5 hours with a feeding rate of 10-12 ml/min, an inlet feeding temperature of 65-110° C. and outlet temperature of 65-75° C. The product was further dried at 60-65° C. for a period of 10.0 h to obtain 38.0 g of Form T1.

Example-12

Preparation of Form T1

To 2100 ml of methanol was added 60.0 g of nebivolol base at room temperature. The pH of reaction mass was adjusted below 2.0 by addition of concentrated HCl (16.20 gm) and stir till clear solution was obtained. Then, the clear solution was spray-dried for a period of 3.5 hours with a feeding rate of 10-12 ml/min, an inlet feeding temperature of 65-110° C. and outlet temperature of 65-75° C. The product was further dried at 60-65° C. for a period of 10.0 h to obtain 38.0 g of Form T1.

X-ray Powder Diffraction Data: provided in Table 1
Preparation of Solid Dosage Form The ingredients used in the preparation of solid dosage form containing nebivolol hydrochloride in the present invention are given below along with the method of preparation. In all the subsequent examples, the dissolution of the prepared tablets was determined in a paddle apparatus. The rotation speed was set at 50±2 revolutions per minute, the dissolution medium being 0.1 N HCl maintained at a fixed temperature of 37° C. (pH 1.2 simulated gastric fluid). The total volume of the dissolution fluid was 500 ml.

Example-13

Preparation of Tablet

The resultant material i.e., nebivolol hydrochloride of example 8 is used for the preparation of solid dosage form in the following examples.

Composition of Tablet

TABLE 3

| Ingredients | Quantity mg/tablet | Percentage by weight |
|---|---|---|
| Nebivolol hydrochloride equivalent to 5 mg of nebivolol | 5.45 | 2.72 |
| Lactose | 125.05 | 62.53 |
| Starch* | 30.00 | 15.00 |
| Croscarmellose sodium | 12.00 | 6.00 |
| Hydroxypropyl methylcellulose (HPMC 6 cps) | 3.00 | 1.50 |
| Microcrystalline cellulose (Avicel PH 102) | 23.00 | 11.50 |
| Magnesium stearate | 1.00 | 0.50 |
| Colloidal silicon dioxide | 0.50 | 0.25 |

*8% (2.4 mg/tablet) extra starch added to compensate moisture loss on drying.

Procedure:

Nebivolol hydrochloride 5.45 mg (2.72% w/w) was sieved through mesh #60, and lactose 125.05 mg (62.53% w/w) croscarmellose sodium 5.00 mg (2.5% w/w) and starch 30.00 mg (15.00% w/w) were all passed through mesh #60. The sifted materials were blended together. 3 mg (1.50% w/w) of hydroxylpropyl methyl cellulose (6 cps) was dissolved in 30 ml of purified water (pre-heated to 70° C.), and was used as the granulating solution to prepare granules of the above blend till the mass of required consistency was obtained. It required 25 ml of extra purified water. The wet mass was passed through mesh #08 and the wet granules dried in a tray dryer at 70° C. till the loss on drying was 1.28%. The dried granules were passed through mesh #20 and blended with a compression mixture comprising of 23.0 mg (11.50% w/w) of microcrystalline cellulose (Avicel PH 102), 0.5 mg (0.25% w/w) of colloidal silicon dioxide, 7.0 mg (3.50% w/w) of croscarmellose sodium and 1.0 mg (0.50% w/w) of magnesium stearate, previously sieved through mesh #60. The final blend thus obtained was compressed into 200 mg tablets on a tablet compression machine using 7.93 mm ($^{10}/_{32}$ inch) round flat bevel edged punches.

Dissolution Profile of Nebivolol Hydrochloride of the Present Invention at pH 1.2 (Simulated Gastric Fluid)

The dissolution of tablets prepared according to the Example-13 is presented in Table 4.

TABLE 4

| SR. NO. | PRODUCT CONTAINING 5 MG UNCOATED TABLET DOSAGE FORM | % DRUG RELEASE AT DIFFERENT TIME INTERVALS | | | |
|---|---|---|---|---|---|
| | | 15 MIN | 30 MIN | 45 MIN | 60 MIN |
| 1. | NEBIVOLOL HYDROCHLORIDE NEBILET ® [REFERENCE] | 84.1 | 93.7 | 97.1 | 98.3 |
| 2. | NEBIVOLOL HYDROCHLORIDE [TEST] | 81.90 | 87.20 | 90.10 | 92.70 |

The reference, i.e., Nebilet® is the nebivolol hydrochloride tablet from the innovator, Janssen Pharmaceutica. The dissolution rate of the tablets prepared in the present invention was found to be more than 75% in 45 minutes. Thus, the dissolution of the tablets prepared according to the present invention is acceptable.

Example-14

Preparation of Tablet

The resultant material i.e., nebivolol hydrochloride of example 8 is used for the preparation of solid dosage form in the following examples.

Composition of Tablet

TABLE 5

| Ingredients | Quantity mg/tablet | Percentage by weight |
|---|---|---|
| Nebivolol hydrochloride (equivalent to 5 mg of nebivolol) | 5.45 | 2.72 |
| Lactose | 125.05 | 62.53 |
| Starch* | 30.00 | 15.00 |
| Croscarmellose sodium | 12.00 | 6.00 |
| Polyvinyl pyrrolidone | 3.00 | 1.50 |
| Microcrystalline cellulose (Avicel PH 102) | 23.00 | 11.50 |

TABLE 5-continued

| Ingredients | Quantity mg/tablet | Percentage by weight |
|---|---|---|
| Magnesium stearate | 1.00 | 0.50 |
| Colloidal silicon dioxide | 0.50 | 0.25 |

*8% (2.4 mg/tablet) extra starch added to compensate moisture loss on drying.

Procedure

Nebivolol hydrochloride 5.45 mg (2.72% w/w) was sieve through mesh #60, and lactose 125.05 mg (62.53% w/w), croscarmellose sodium 5.00 mg (2.5% w/w) and starch 30.00 mg (15.00% w/w) were all passed through mesh #60. The sifted materials were blended together. 3 mg (1.50% w/w) of polyvinyl pyrrolidone K-30 were dissolved in 30 ml of purified water pre-heated to 70° C., and was used as the granulating solution to prepare granules of the above blend till the mass of required consistency was obtained. It required 25 ml of extra purified water. The wet mass was passed through mesh #08 and the wet granules dried in a tray dryer at 70° C. till the loss on drying was 1.258%. The dried granules were passed through mesh #20 and blended with a compression mixture comprising of 23.0 mg (11.50% w/w) of microcrystalline cellulose (Avicel PH 102), 0.5 mg (0.25% w/w) of colloidal silicon dioxide, 7.0 mg (3.5% w/w) of croscarmellose sodium and 1.0 mg (0.50% w/w) of magnesium stearate, previously sieved through mesh #60. The final blend thus obtained was compressed into 200 mg tablets on a tablet compression machine using 7.93 mm ($^{10}/_{32}$ inch) round flat bevel edged punches.

Dissolution Profile of Nebivolol Hydrochloride of the Present Invention at pH 1.2 (Simulated Gastric Fluid)

The dissolution of tablets prepared according to the Example-14 is presented in Table 6.

TABLE 6

| SR NO. | PRODUCT CONTAINING 5 MG UNCOATED TABLET DOSAGE FORM | % DRUG RELEASE AT DIFFERENT TIME INTERVALS | | | |
|---|---|---|---|---|---|
| | | 15 MIN | 30 MIN | 45 MIN | 60 MIN |
| 1. | NEBIVOLOL HYDROCHLORIDE; NEBILET ® [REFERENCE] | 84.1 | 93.7 | 97.1 | 98.3 |
| 2. | NEBIVOLOL HYDROCHLORIDE [TEST] | 89.00 | 95.00 | 97.20 | 98.00 |

The reference, i.e., Nebilet® is the nebivolol hydrochloride tablet from the innovator, Janssen Pharmaceutica. The dissolution rate of the tablets prepared in the present invention were found to be more than 75% in 45 minutes. Thus, the dissolution of the tablets prepared according to the present invention is acceptable.

Example-15

Preparation of Tablet

The resultant material i.e., nebivolol hydrochloride of example 7 is used for the preparation of solid dosage form in the following examples.

Preparation of Tablets by Wet Granulation Method (Drug being Adsorbed onto the Excipients).

The ingredients used in the preparation of tablets containing nebivolol hydrochloride in the present invention by adsorption of drug onto the excipients and subsequent wet granulation method are given below along with the method of preparation of said tablets.

Step A: Formula for Drug Adsorption on to the Excipients

TABLE 7

| Ingredients | Quantity in mg/Tablet | Percentage by weight |
|---|---|---|
| Nebivolol hydrochloride equivalent to 5 mg of nebivolol (crystalline) | 5.45 | 2.86 |
| Lactose | 144.62 | 75.99 |
| Starch* | 34.50 | 18.13 |
| Croscarmellose sodium | 5.75 | 3.02 |
| Methanol | — | |

*8% extra starch added to compensate moisture loss on drying.

Procedure

Nebivolol hydrochloride 5.45 mg (2.86% w/w) (2% extra to compensate for loss) was added to a solution of methanol 2780 ml with stirring (1% w/v drug solution in methanol) passed lactose 144.62 mg (75.99% w/w), croscarmellose sodium 28.75 mg (3.02% w/w) and starch 34.5 mg (18.13% w/w) through mesh #60. The sifted materials were blended together. This combined blend was added to the fluidization pan and the drug solution was adsorbed on it by using Fluid bed processor (top spray process).

Step B: Preparation of Tablets by Wet Granulation Method

The ingredients used in the preparation of tablets containing nebivolol hydrochloride in the present invention by wet granulation method are given below along with the method of preparation of said tablets.

TABLE 8

| Ingredients | Quantity mg/tablet | Percentage by weight |
|---|---|---|
| Nebivolol hydrochloride adsorbed on blend of step A | 190.325 | 82.75 |
| Hydroxypropyl methyl cellulose (HPMC 6 cps) | 3.45 | 1.50 |
| Croscarmellose sodium | 8.05 | 3.50 |
| Microcrystalline cellulose (Avicel PH 102) | 26.45 | 11.50 |
| Magnesium stearate | 1.15 | 0.50 |
| Colloidal silicon dioxide | 0.575 | 0.25 |

Procedure 3.45 mg (1.50% w/w) of hydroxypropyl methyl cellulose (6 cps) were dissolved in 35 ml of purified water pre-heated to 70° C. and then after cooled, and is used as the granulating solution to prepare granules by mixing with nebivolol hydrochloride adsorbed blend till the mass of required consistency was obtained. It required 25 ml of extra purified water. The wet mass was dried in a tray dryer at 70° C. till the loss on drying was 1.48%. The dried granules were sieved through mesh #20 and blended with a lubricants comprising of 26.45 mg (11.50% w/w) of microcrystalline cellulose (Avicel PH 102), 0.575 mg (0.25% w/w) of colloidal silicon dioxide, 8.05 mg (3.50% w/w) of croscarmellose sodium and 1.15 mg (0.50% w/w) of magnesium stearate, previously sieved through mesh #60. The final blend thus obtained was compressed into 230 mg average weight tablets on a tablet compression machine using 8.73 mm (11/32 inch) round flat-faced beveled edged punches.

Dissolution Profile of Nebivolol Hydrochloride of the Present Invention at pH 1.2 (Simulated Gastric Fluid)

The dissolution of tablets prepared according to the Example-15 is presented in Table 9.

TABLE 9

| PRODUCT CONTAINING 5 MG UNCOATED TABLET | | % DRUG RELEASE AT DIFFERENT TIME INTERVALS | | | |
|---|---|---|---|---|---|
| SR NO. | DOSAGE FORM | 15 MIN | 30 MIN | 45 MIN | 60 MIN |
| 1. | NEBIVOLOL HYDROCHLORIDE; NEBILET ® [REFERENCE] | 84.1 | 93.7 | 97.1 | 98.3 |
| 2. | NEBIVOLOL HYDROCHLORIDE [TEST] | 86.9 | 90.1 | 92.6 | 93.2 |

Example-16

Preparation of Tablet

The resultant material i.e., nebivolol hydrochloride of example 8 is used for the preparation of solid dosage form in the following examples.

Composition of Tablet

TABLE 10

| Ingredient | Quantity mg/Tab | Percentage by Weight |
|---|---|---|
| Nebivolol Hydrochloride | 5.45 | 2.73 |
| Lactose | 158.05 | 79.03 |
| Croscarmellose sodium | 12 | 6.00 |
| Microcrystalline Cellulose | 23 | 11.50 |
| Colloidal Silicon Dioxide | 0.5 | 0.25 |
| Magnesium stearate | 1 | 0.50 |

Procedure:

Nebivolol hydrochloride 5.45 mg (2.72% w/w) was sieve through mesh #60, and lactose 158.05 mg (79.03% w/w) and croscarmellose sodium 5.00 mg (2.5% w/w) were all passed through mesh #60. The sifted materials were blended together. 35 ml of purified water was used as the granulating solution to prepare granules of the above blend till the mass of required consistency was obtained. The wet mass was passed through mesh #08 and the wet granules dried in a tray dryer at 70° C. till the loss on drying was 0.65%. The dried granules were passed through mesh #20 and blended with a compression mixture comprising of 23.0 mg (11.50% w/w) of microcrystalline cellulose, 0.5 mg (0.25% w/w) of colloidal silicon dioxide, 7.0 mg (3.5% w/w) of croscarmellose sodium and 1.0 mg (0.50% w/w) of magnesium stearate, previously sieved through mesh #60. The final blend thus obtained was compressed into 200 mg tablets on a tablet compression machine using 7.93 mm (10/32 inch) round flat bevel edged punches.

Dissolution Profile of Nebivolol Hydrochloride of the Present Invention at pH 1.2 (Simulated Gastric Fluid)

The dissolution of tablets prepared according to the Example-16 is presented in Table 11.

TABLE 11

| PRODUCT CONTAINING 5 MG UNCOATED TABLET | | % DRUG RELEASE AT DIFFERENT TIME INTERVALS | | | |
|---|---|---|---|---|---|
| SR. NO. | DOSAGE FORM | 15 MIN | 30 MIN | 45 MIN | 60 MIN |
| 1. | NEBIVOLOL HYDROCHLORIDE; NEBILET ® [REFERENCE] | 84.1 | 93.7 | 97.1 | 98.3 |
| 2. | NEBIVOLOL HYDROCHLORIDE [TEST] | 92.1 | 94.7 | 95.8 | 96.3 |

The reference, i.e., Nebilet® is the nebivolol hydrochloride tablet from the innovator, Janssen Pharmaceutica. The dissolution rate of the tablets prepared in the present invention was found to be more than 75% in 45 minutes. Thus, the dissolution of the tablets prepared according to the present invention is acceptable.

Example-17

Preparation of Tablet

The resultant material i.e., nebivolol hydrochloride of example 7 is used for the preparation of solid dosage form in the following examples.
Composition of Tablet

TABLE 12

| Ingredient | Quantity mg/Tab | Percentage by weight |
|---|---|---|
| Nebivolol Hydrochloride | 5.45 | 2.41 |
| Lactose | 179.125 | 79.07 |
| Croscarmellose sodium | 13.8 | 6.09 |
| Microcrystalline Cellulose | 26.45 | 11.68 |
| Colloidal Silicon Dioxide | 0.575 | 0.25 |
| Magnesium stearate | 1.15 | 0.51 |

Procedure

Nebivolol hydrochloride 5.45 mg (2.41% w/w) was added to methanol with stirring (1% w/v drug solution in methanol). Passed lactose 179.125 mg (79.07% w/w) through mesh #60. This blend was added to the fluidization pan and the drug solution was adsorbed on it by using fluid bed process (top spray process).
Preparation of Tablets by Wet Granulation Method The ingredients used in the preparation of tablets containing nebivolol hydrochloride in the present invention by wet granulation method are given below along with the method of preparation of said tablets.
Procedure Purified water was used as the granulating solution to prepare granules by mixing with nebivolol hydrochloride adsorbed blend till the mass of required consistency was obtained. The wet mass was dried in a tray dryer at 70° C. till the loss on drying was 0.71%. The dried granules were sieved through mesh #20 and blended with a lubricants comprising of 26.45 mg (11.67% w/w) of microcrystalline cellulose, 0.575 mg (0.25% w/w) of colloidal silicon dioxide, 13.8 mg (6.09% w/w) of croscarmellose sodium and 1.15 mg (0.51% w/w) of magnesium stearate, previously sieved through mesh #60. The final blend thus obtained was compressed into 226.55 mg average weight tablets on a tablet compression machine using 8.73 mm (11/32 inch) round flat faced beveled edged punches.
Dissolution Profile of Nebivolol Hydrochloride of the Present Invention at pH 1.2 (Simulated Gastric Fluid)

The dissolution of tablets prepared according to the Example-17 is presented in Table-13.

TABLE 13

| PRODUCT CONTAINING 5 MG UNCOATED TABLET | | % DRUG RELEASE AT DIFFERENT TIME INTERVALS | | | |
|---|---|---|---|---|---|
| SR NO. | DOSAGE FORM | 15 MIN | 30 MIN | 45 MIN | 60 MIN |
| 1. | NEBIVOLOL HYDROCHLORIDE; NEBILET ® [REFERENCE] | 84.1 | 93.7 | 97.1 | 98.3 |
| 2. | NEBIVOLOL HYDROCHLORIDE [TEST] | 95.5 | 95.4 | 95.4 | 95.7 |

Example 18

Preparation of Tablet

The resultant material i.e., nebivolol hydrochloride of example 8 is used for the preparation of solid dosage form in the following examples.
Composition of Tablet

TABLE 14

| Ingredient | Quantity mg/Tab | Percentage by weight |
|---|---|---|
| Nebivolol Hydrochloride | 5.450 | 2.73 |
| Lactose | 170.050 | 85.03 |
| Microcrystalline Cellulose | 23.000 | 11.50 |
| Colloidal Silicon Dioxide | 0.500 | 0.25 |
| Magnesium stearate | 1.000 | 0.50 |

Procedure:

Nebivolol hydrochloride 5.45 mg (2.73% w/w) and lactose 170.05 mg (85.03% w/w) were all passed through mesh #60. The sifted materials were blended together. 35 ml of purified water was used as the granulating solution to prepare granules of the above blend till the mass of required consistency was obtained. The wet mass was passed through mesh #08 and the wet granules dried in a tray dryer at 70° C. till the loss on drying was 0.39%. The dried granules were passed through mesh #20 and blended with a compression mixture comprising of 23.0 mg (11.5% w/w) of microcrystalline cellulose, 0.5 mg (0.25% w/w) of colloidal silicon dioxide and 1.0 mg (0.50% w/w) of magnesium stearate, previously sieved through mesh #60. The final blend thus obtained was compressed into 200 mg tablets on a tablet compression machine using 7.93 mm (10/32 inch) round flat bevel edged punches.

Dissolution Profile of Nebivolol Hydrochloride of the Present Invention at pH 1.2 (Simulated Gastric Fluid)

The dissolution of tablets prepared according to the Example-18 is presented in Table 15.

TABLE 15

| PRODUCT CONTAINING 5 MG UNCOATED TABLET | | % DRUG RELEASE AT DIFFERENT TIME INTERVALS | | | |
|---|---|---|---|---|---|
| SR. NO. | DOSAGE FORM | 15 MIN | 30 MIN | 45 MIN | 60 MIN |
| 1. | NEBIVOLOL HYDROCHLORIDE; NEBILET ® [REFERENCE] | 84.1 | 93.7 | 97.1 | 98.3 |
| 2. | NEBIVOLOL HYDROCHLORIDE [TEST] | 89.5 | 94.2 | 96.2 | 97.1 |

The reference, i.e., Nebilet® is the nebivolol hydrochloride tablet from the innovator, Janssen Pharmaceutica. The dissolution rate of the tablets prepared in the present invention was found to be more than 75% in 45 minutes. Thus, the dissolution of the tablets prepared according to the present invention is acceptable.

Example-19

Preparation of Tablet

The resultant material i.e., nebivolol hydrochloride of example 8 is used for the preparation of solid dosage form in the following examples.
Composition of Tablet

TABLE 16

| Ingredient | Quantity mg/Tab | Percentage by weight |
|---|---|---|
| Nebivolol Hydrochloride | 5.450 | 2.56 |
| Lactose | 179.125 | 84.20 |
| Microcrystalline Cellulose | 26.450 | 12.43 |
| Colloidal Silicon Dioxide | 0.575 | 0.27 |
| Magnesium stearate | 1.150 | 0.54 |

Procedure

Nebivolol hydrochloride 5.45 mg (2.56% w/w) was added to methanol with stirring (1% w/v drug solution in methanol). 179.125 mg of lactose (84.20% w/w) was passed through mesh #60. This blend was added to the fluidization pan and the drug solution was adsorbed on it by using fluid bed processor (top spray process).
Preparation of Tablets by Wet Granulation Method The ingredients used in the preparation of tablets containing nebivolol hydrochloride in the present invention by wet granulation method are given below along with the method of preparation of said tablets.
Procedure 50 ml of purified water is used as the granulating solution to prepare granules by mixing with nebivolol hydrochloride adsorbed blend till the mass of required consistency was obtained. The wet mass was dried in a tray dryer at 70° C. till the loss on drying was 1.12%. The dried granules were sieved through mesh #20 and blended with a lubricants comprising of 26.45 mg (12.43% w/w) of microcrystalline cellulose, 0.575 mg (0.27% w/w) of colloidal silicon dioxide and 1.15 mg (0.54% w/w) of magnesium stearate previously sieved through mesh #60. The final blend thus obtained was compressed into 212.75 mg average weight tablets on a tablet compression machine using 8.73 mm (¹¹/₃₂ inch) round flat faced beveled edged punches.
Dissolution Profile of Nebivolol Hydrochloride of the Present Invention at pH 1.2 (Simulated Gastric Fluid)

The dissolution of tablets prepared according to the Example-1.9 is presented in Table 17.

TABLE 17

| PRODUCT CONTAINING 5 MG UNCOATED TABLET | | % DRUG RELEASE AT DIFFERENT TIME INTERVALS | | | |
|---|---|---|---|---|---|
| SR. NO. | DOSAGE FORM | 15 MIN | 30 MIN | 45 M1N | 60 MIN |
| 1. | NEBIVOLOL HYDROCHLORIDE; NEBILET ® [REFERENCE] | 84.1 | 93.7 | 97.1 | 98.3 |
| 2. | NEBIVOLOL HYDROCHLORIDE [TEST] | 85.0 | 93.9 | 96.5 | 97.9 |

The reference, i.e., Nebilet® is the nebivolol hydrochloride tablet from the innovator, Janssen Pharmaceutica. The dissolution rate of the tablets prepared in the present invention was found to be more than 75% in 45 minutes. Thus, the dissolution of the tablets prepared according to the present invention is acceptable.

Example-20

Preparation of Tablet

The resultant material i.e., nebivolol hydrochloride of example 10 is used for the preparation of solid dosage form in the following examples.
Composition of Tablet

TABLE 18

| Ingredient | Quantity mg/Tablet | Percentage by weight |
|---|---|---|
| Lactose Monohydrate (Pharmatose 200M) | 143.475 | 62.38 |
| Maize Starch | 34.50 | 15.00 |
| Croscarmellose Sodium (AC-DI-SOL) | 6.90 | 3.00 |
| Nebivolol Hydrochloride | 5.45 | 2.37 |
| Methanol | | |
| Hypromellose (6 cps) | 3.45 | 1.50 |
| Purified Water | | |
| Croscarmellose Sodium (AC-DI-SOL) | 6.90 | 3.00 |
| Cellulose Microcrystalline (Avicel PH102) | 26.45 | |
| Silica Colloidal Anhydrous | 0.575 | 0.25 |
| Magnesium Stearate | 2.30 | 1.00 |

Procedure:

A solution of 5.45 mg (2.37% w/w) of nebivolol hydrochloride and 3.45 mg (1.5% w/w) of hypromellose was prepared in 440 mg of methanol and 10 mg of water. Lactose 143.475 mg (62.38% w/w), maize starch 34.50 mg (15% w/w) (8% extra added to compensate the loss) and croscarmellose sodium 3.45 mg (3% w/w) were sifted through mesh #40. The sifted materials were loaded to product container of Fluid Bed Processor (FBP). The solution of nebivolol hydrochloride—hypromellose was adsorbed onto the blend fluidized in the container of the fluid Bed Processor by top spay process. The blend was dried after completion of adsorption of Drug-binder solution. The blend was then granulated with 28 mg water. The wet granules were dried in the Fluid Bed Processor at 60° C. The dried granules were sieved through mesh #30 and blended with microcrystalline cellulose 26.45 mg (11.5% w/w), croscarmellose Sodium 3.45 mg (3% w/w), colloidal silicon dioxide 0.575 mg (0.25% w/w) pre-sifted through mesh #40 and pre-sifted magnesium stearate 2.30 mg (1% w/w). The final blend thus obtained was compressed into 230 mg average weight tablets on a tablet compression machine using 9.0 mm round concave beveled edged punches having scored on one side.

Dissolution Profile of Nebivolol Hydrochloride of the Present Invention at pH 1.2 (Simulated Gastric Fluid)

The dissolution of tablets prepared according to the Example-20 is presented in Table 19.

TABLE 19

| SR. NO. | PRODUCT CONTAINING 5 MG UNCOATED TABLET DOSAGE FORM | % DRUG RELEASE AT DIFFERENT TIME INTERVALS | | | |
|---|---|---|---|---|---|
| | | 15 MIN | 30 MIN | 45 MIN | 60 MIN |
| 1. | NEBIVOLOL HYDROCHLORIDE; NEBILET ® [REFERENCE] | 84.20 | 90.00 | 91.40 | 92.10 |
| 2. | NEBIVOLOL HYDROCHLORIDE [TEST] | 88.70 | 93.60 | 94.10 | 94.70 |

Example-21

Comparative Bioavailability Data of Nebivolol Tablet of Instant Invention (Test Formulation) v/s Nebilet Tablet (Reference Formulation)

Pharmacokinetics

In a bioequivalence study, 24 healthy human volunteers were enrolled and randomised to receive the test (nebivolol 5 mg of Torrent Pharmaceuticals Ltd., India) or reference (Nebilet® 5 mg of Berlin-Chemie AG, Germany) formulations. The plasma levels of nebivolol were measured by using a validated LCMS/MS method.

The mean plasma concentrations of nebivolol after an oral dose of 1 tablet (5 mg nebivolol) of the test formulation or 1 tablet (5 mg nebivolol) of the reference formulation are plotted in figure-VI.

The pharmacokinetic parameters were evaluated. For nebivolol test & reference formulations the mean $C_{max}$ achieved was 2.605±0.66 ng/ml and 2.574±0.78 ng/ml respectively. There was no major difference in the mean $t_{max}$ for both test and reference formulations. The observed mean $AUC_{(0-t)}$ for test and reference formulations was 17.33±29.54 ng·h/ml and 17.71±30.77 ng·h/ml respectively. The observed mean $AUC_{(0-\infty)}$ for test and reference formulations was 29.69±62.72 ng·h/ml and 21.86±41.96 ng·h/ml respectively.

The 90%-confidence interval calculated by means of ANOVA-log for the primary parameter, intra-individual ratio (T/R) of $AUC_{(0-t)}$, $AUC_{(0-\infty)}$ and $C_{max}$ of nebivolol was 0.93-1.04, 0.95-1.17 and 0.95-1.10.

Safety

The drug was well tolerated. No adverse events were reported in any volunteer in the trial. The laboratory results gave no indications for adverse events or adverse drug reactions.

CONCLUSION

The above-mentioned pharmacokinetic parameters for nebivolol of the test (nebivolol 5 mg of Torrent Pharmaceuticals Ltd., India) and reference (Nebilet® 5 mg of Berlin-Chemie AG, Germany) formulation were bioequivalent with respect to nebivolol as shown in Table 20.

TABLE 20

| Formulation | Mean $C_{max}$ (ng/ml) | Mean $AUC_{(0-t)}$ (ng/ml * hr) | Mean $AUC_{(0-\infty)}$ (ng/ml * hr) |
|---|---|---|---|
| Nebivolol 5 mg of Torrent Pharmaceuticals Ltd., India | 2.605 ± 0.66 | 17.33 ± 29.54 | 29.69 ± 62.72 |
| Nebilet ® 5 mg of Berlin-Chemie AG, Germany | 2.574 ± 0.78 | 17.714 ± 30.77 | 21.86 ± 41.96 |

$C_{max}$ - The peak plasma concentration achieved after the administration of the drug.
AUC—Area under the curve

The invention claimed is:

1. A pharmaceutical composition comprising nebivolol hydrochloride and a pharmaceutically acceptable carrier, characterized in that said pharmaceutical composition does not contain a wetting agent, and optionally contains a binder and/or a disintegrant, wherein the pharmaceutical composition has a dissolution in 0.1 N HCl of more than 75% in 45 minutes.

2. The pharmaceutical composition as claimed in claim 1, wherein said pharmaceutical composition is a tablet or a capsule.

3. The tablet as claimed in claim 2, having the following composition:

| | |
|---|---|
| Nebivolol Hydrochloride | 2.37% w/w |
| Lactose Monohydrate | 62.38% w/w |
| Maize Starch | 15.00% w/w |
| Croscarmellose Sodium | 6.00% w/w |
| Hypromellose (6 cps) | 1.50% w/w |
| Microcrystalline Cellulose | 11.50% w/w |
| Silica Colloidal Anhydrous | 0.25% w/w |
| Magnesium Stearate | 1.00% w/w. |

4. The pharmaceutical composition as claimed in claim 1, wherein the nebivolol hydrochloride is present in an amount of 0.5% to 10% w/w; the composition further comprises a diluent, a lubricant and a glidant; the diluent is present in an amount of 78% to 93.05% w/w; the lubricant is present in an amount of 0.25% to 3% w/w; and the glidant is present in an amount of 0.25% to 3% w/w; and optionally, the binder is present in an amount of 0.5% to 5% w/w and/or the disintegrant is present in an amount of 0.5% to 10% w/w.

5. The pharmaceutical composition as claimed in claim 1, wherein the pharmaceutically acceptable carrier is at least one selected from the group consisting of a diluent, a lubricant and a glidant.

6. The pharmaceutical composition as claimed in claim 5, wherein the diluent is at least one selected from the group consisting of lactose, starch, dibasic calcium phosphate anhydrous, tribasic calcium phosphate, kaolin, sucrose, mannitol, precipitated calcium carbonate, sorbitol, maltodextrin, and cellulose derivatives including powdered cellulose and micro crystalline cellulose, the binder is at least one selected from the group consisting of hydroxypropylmethylcellulose, acacia, alginic acid, hydroxy propyl cellulose, carboxymethylcellulose sodium, compressible sugar, ethylcellulose, gelatin, liquid glucose, methylcellulose and pregelatinized starch, the disintegrant is at least one selected from the group consisting of starch, croscarmellose sodium, crospovidone, alginic acid, carboxymethyl cellulose sodium and guar gum, the lubricant is at least one selected from the group consisting of stearic acid, polyethylene glycol, magnesium stearate, calcium stearate, talc, zinc stearate, hydrogenated castor oil, silica, colloidal silica, cornstarch, calcium silicate, magnesium silicate and silicon hydrogel, the glidant is at least one selected from the group consisting of colloidal silicon dioxide, colloidal silica, cornstarch, talc, calcium silicate, magnesium silicate, colloidal silicon, and silicon hydrogel.

* * * * *